(12) United States Patent
Rabbani et al.

(10) Patent No.: US 10,646,459 B2
(45) Date of Patent: May 12, 2020

(54) SPHINGOSINE PATHWAY MODULATING COMPOUNDS FOR THE TREATMENT OF CANCERS

(71) Applicant: Enzo Biochem, Inc., New York, NY (US)

(72) Inventors: Elazar Rabbani, New York, NY (US); James J. Donegan, Long Beach, NY (US)

(73) Assignee: Enzo Biochem, Inc., New York, NY (US)

( * ) Notice: Subject to any disclaimer, the term of this patent is extended or adjusted under 35 U.S.C. 154(b) by 0 days.

(21) Appl. No.: 16/287,201

(22) Filed: Feb. 27, 2019

(65) Prior Publication Data

US 2019/0192451 A1    Jun. 27, 2019

Related U.S. Application Data

(62) Division of application No. 16/017,345, filed on Jun. 25, 2018, now Pat. No. 10,278,960.

(60) Provisional application No. 62/524,221, filed on Jun. 23, 2017.

(51) Int. Cl.
| | |
|---|---|
| *A61K 31/137* | (2006.01) |
| *A61K 31/4245* | (2006.01) |
| *A61K 45/06* | (2006.01) |
| *A61K 31/135* | (2006.01) |
| *A61P 35/00* | (2006.01) |
| *A61P 35/02* | (2006.01) |

(52) U.S. Cl.
CPC .......... *A61K 31/137* (2013.01); *A61K 31/135* (2013.01); *A61K 31/4245* (2013.01); *A61K 45/06* (2013.01); *A61P 35/00* (2018.01); *A61P 35/02* (2018.01); *A61K 2300/00* (2013.01)

(58) Field of Classification Search
USPC ...................................................... 514/364
See application file for complete search history.

(56) References Cited

U.S. PATENT DOCUMENTS

| | | | |
|---|---|---|---|
| 2,868,844 A | 1/1959 | Coffield et al. | |
| 3,871,958 A | 3/1975 | Nakazawa et al. | |
| 4,707,440 A | 11/1987 | Stavrianopoulos et al. | |
| 6,372,800 B1 | 4/2002 | Fujita et al. | |
| 7,338,961 B2 | 3/2008 | Smith et al. | |
| 8,314,151 B2 | 11/2012 | Spiegel et al. | |
| 8,372,888 B2 | 2/2013 | Zipkin et al. | |
| 9,388,121 B2 | 7/2016 | Spiegel | |
| 9,974,755 B2 | 5/2018 | Alonso et al. | |
| 2004/0203104 A1 | 10/2004 | Spiegel et al. | |
| 2007/0196493 A1 | 8/2007 | Kinski et al. | |
| 2007/0275908 A1 | 11/2007 | Defrees | |
| 2008/0145883 A1 | 6/2008 | Baumruker et al. | |
| 2008/0167352 A1 | 7/2008 | Smith et al. | |
| 2009/0318389 A1 | 12/2009 | Evindar et al. | |
| 2010/0035959 A1 | 2/2010 | Zipkin et al. | |
| 2010/0056762 A1 | 3/2010 | Old | |
| 2010/0233121 A1 | 9/2010 | Frohna | |
| 2011/0172202 A1 | 7/2011 | Martinborough et al. | |
| 2013/0231326 A1 | 9/2013 | Martinborough et al. | |
| 2014/0271824 A1 | 9/2014 | Kesler et al. | |
| 2015/0299149 A1 | 10/2015 | Martinborough et al. | |

FOREIGN PATENT DOCUMENTS

| | | |
|---|---|---|
| WO | WO2006/004359 | 1/2006 |
| WO | WO 2011/005290 | 1/2011 |
| WO | WO2011/005290 | 1/2011 |
| WO | WO2011/025545 | 3/2011 |
| WO | WO2017/129769 | 8/2017 |
| WO | WO2018/035292 | 2/2018 |
| WO | WO2018/093591 | 5/2018 |

OTHER PUBLICATIONS

Scott et. al. in British Journal of Pharmacology (2016) 173:1778-1792 (Year: 2016).*
International Search Report for copending PCT Application No. PCT/US2018/067131.
Venkatesan et al., Preclinical evaluation of Ozanimod for prostate cancer treatment [abstract], in: Proceedings of the American Association for Cancer Research Annual Meeting 2019; Mar. 29-Apr. 3, 2019; Atlanta, GA Philadelphia (PA): AACR; Cancer Res. 2019;79(13 Suppl); Abstract nr 2974.
Anelli et al., Sphingosine kinase 1 is up-regulated during hypoxia in U87MG glioma cells, JBC 2008, 3365-3375, 283.
Barthwal et al., Negative regulation of mixed lineage kinase 3 by protein kinase B/AKT leads to cell survival, JBC 2003, 3897-3902, 278.
Coward et al., Safingol (L-threo-sphinganine) induces autophagy in solid tumor cells through inhibition of PKC and the PI3-kinase pathway, Autophagy 2009, 184-193, 5.
Cuvillier et al., Downregulating sphingosine kinase-1 for cancer therapy, Expert. Opin. Ther. Targets 2008, 1009-1020, 12.
Giannini et al., Patient tumor EGFR and PDGFRA gene amplifications retained in an invasive intracranial xenograft model of glioblastoma multiforme, Neuro-Oncology 2005, 164-176, 7.
Giussani et al., Phosphatidylinositol 3-kinase/AKT pathway regulates the endoplasmic reticulum to golgi traffic of ceramide in glioma cells, JBC 2009, 5088-5096, 284.
Haas-Kogan et al., Protein kinase B (PKB/AKT) activity is elevated in glioblastoma cells due to mutation of the tumor suppressor PTEN/MMAC, Current Biology 1998, 1195-1198, 8.
Hannun and Obeid, Principles of bioactive lipid signalling: lessons from sphingolipids, Nature Reviews Molecular Cell Biology 2008, 139-150, 9.
Kim et al., Akt phosphorylates and negatively regulates apoptosis signal-regulating kinase 1, Molecular and Cellular Biology 2001, 893-901, 21.

(Continued)

*Primary Examiner* — Marcos L Sznaidman

(74) *Attorney, Agent, or Firm* — Paul Diamond, Esq.

(57) ABSTRACT

The invention provides methods and compositions for treating cancers and myeloproliferative disorders using sphingosine kinase-1 inhibitors, such as SK1-I, and selective sphingosine-1-phosphate receptor agonists, such as ozanimod.

4 Claims, 21 Drawing Sheets

(56) References Cited

OTHER PUBLICATIONS

Kusner et al., The localization and activity of sphingosine kinase 1 are coordinately regulated with actin cytoskeletal dynamics in macrophages, JBC 2007, 23147-23162, 282.
Lepley et al., The G protein-coupled receptor S1P2 regulates Rho/Rho kinase pathway to inhibit tumor cell migration Cancer Res. 2005, 3788-3795, 65.
Le Scolan et al., Overexpression of sphingosine kinase 1 is an oncogenic event in erythroleukemic progression, Blood 2005, 1808-1816, 106.
Li et al., Clinical significance of sphingosine kinase-1 expression in human astrocytomas progression and overall patient survival, Clin. Cancer Res. 2008, 6996-7003, 14.
Maceyka et al. Filamin A links sphingosine kinase 1 and sphingosine-1-phosphate receptors 1 at lamellipodia to orchestrate cell migration, Molecular Cellular Biology 2008, 5687-5697 28.
Maher et al., Malignant glioma: genetics and biology of a grave matter, Genes Dev. 2001, 1311-1333, 15.
Malchinkhuu et al., Role of p38 mitogen-activated kinase and c-Jun terminal kinase in migration response to lysophosphatidic acid and sphingosine-1-phosphate in glioma cells, Oncogene 2005, 6676-6688, 24.
Mattoon et al., The docking protein Gab1 is the primary mediator of EGF-stimulated activation of the PI-3K/Akt cell survival pathway, BMC Biology 2004, 24-35, 2.
Merrill et al., Sphingolipidomics: high-throughput, structure-specific, and quantitative analysis of sphingolipids by liquid chromatography tandem mass spectrometry, Methods 2005, 207-224, 36.
Murph and Mills, Targeting the lipids LPA and S1P and their signalling pathways to inhibit tumour progression, Expert Rev Mol Med 2007. 1-18, 9.
Nakamizo et al., Human bone marrow-derived mesenchymal stem cells in the treatment of gliomas, Cancer Res 2005, 3307-3318, 65.
Olivera et al., Sphingosine kinase type 1 induces G12/13-mediated stress fiber formation, yet promotes growth and survival independent of G protein-coupled JBC 2003, 46452-46460 278.
Paugh et al., A selective sphingosine kinase 1 inhibitor integrates multiple molecular therapeutic targets in human leukemia, Blood 2008, 1382-1391, 112.
Pchejetski et al., Sphingosine kinase-1 as a chemotherapy sensor in prostate adenocarcinoma cell and mouse models Cancer Res. 2005, 11667-11675, 65.
Qu et al., Iodophenyl tagged sphingosine derivatives: synthesis and preliminary biological evaluation, Bioorg & Med Chem Lett 2009, 3382-3385, 19.
Radeff-Huang et al., Tumor necrosis factor-alpha-stimulated cell proliferation is mediated through sphingosine kinase-dependent Akt activation and cyclin D expression, JBC 2007, 863-870, 282.
Riboni et al., Ceramide levels are inversely associated with malignant progression of human glial tumors, Glia 2002, 105-113, 39.
Sankala et al., Involvement of sphingosine kinase 2 in p53-independent induction of p21 by the chemotherapeutic drug doxorubicin, Cancer Res. 2007, 10466-10474, 67.
Shida et al., Cross-talk between LPA1 and epidermal growth factor receptors mediates up-regulation of sphingosine kinase 1 to promote gastric cancer cell motility and invasion, Cancer Res. 2008, 6569-6577, 68.
Shida et al., Targeting SphK1 as a new strategy against cancer, Current Drug Targets 2008, 662-673, 9.
Stommel et al., Coactivation of receptor tyrosine kinases affects the response of tumor cells to targeted therapies, Science 2007, 287-290, 318.
Wen et al., Malignant gliomas in adults, N. Engl J. Med. 2008, 492-507, 359.
Van Brocklyn et al., Sphingosine-1-phosphate stimulates human glioma cell proliferation through Gi-coupled receptors: role of ERK MAP kinase and phosphatidylinositol 3-kinase beta, Cancer Lett 2002, 195-204, 181.
Van Brocklyn et al., Sphingosine-1-phosphate stimulates motility and invasiveness of human glioblastoma multiforme cells, Cancer Lett 2003, 53-60, 199.
Van Brocklyn et al., Sphingosine kinase-1 expression correlates with poor survival of patients with glioblastoma multiforme: roles of sphingosine kinase isoforms in growth of glioblastoma cell lines, J Neuropathol Exp Neurol 2005, 695-705, 64.
Xia et al., Opposing effects of ERK and JNK-p38 MAP kinases on apoptosis, Science 1995, 1326-1331, 270.
Yacoub et al., MDA-7 regulates cell growth and radiosensitivity in vitro of primary (non-established) human glioma cells, Cancer Biology & Therapy 2004, 739-751, 3.
Yacoub et al., MDA-7/IL-24 plus radiation enhance survival in animals with intracranial primary human GBM tumors Cancer Biology & Therapy 2008, 917-933, 7.
Yacoub et al., Regulation of GST-MDA-7 toxicity in human glioblastoma cells by ERBB1, ERK1/2, PI3K, and JNK1-3 pathway signaling, Mol Cancer Ther 2008, 314-329, 7.
Young et al., Rolse of sphingosine-1-phosphate (S1P) receptors in malignant behavior of glioma cells. Differential effects of S1P2 on cell migration and invasiveness, Exp Cell Res. 2007, 1615-1627, 313.
Amarente-Mendes et al., Bcr-Abl exerts its antiapoptotic effect against diverse apoptotic stimuli through blockage of mitochondrial release of cytochrome C and activation of caspase-3, Blood 1998, 1700-1705, 91.
Baran et al., Alterations of ceramide/sphingosine 1-phosphate rheostat involved in the regulation of resistance to imatinib-induced apoptosis in k562 human chronic myeloid luekemia cells, JBC 2007, 10922-10934, 282.
Berdyshev et al., De novo biosynthesis of dihydrosphingosine-1-phosphate by sphingosine kinase 1 in mammalian cells, Cell Signal 2006, 1779-1792, 18.
Betito et al., Regulation by sphingosine-1-phosphate of Bax and Bad activities during apoptosis in a MEK-dependent manner, Biochem Biophys Res Commun 2006, 1273-1277, 340.
Bonhoure et al., Overcoming MDR-associated chemoresistance in HL-60 acute myeloid leukemia cells by targeting sphingosine kinase-1, Leukemia 2006, 95-102, 20.
Brinkman, Volker, Sphingosine 1-phosphate receptors in health and disease: mechanistic insights from gene deletion studies and reverse pharmacology, Pharmacol Ther 2007, 85-105, 115.
Cheng et al., Conversion of Bcl-2 to a Bax-like death effector by caspases, Science 1997, 1966-1968, 278.
Cuvillier et al., Suppression of ceramide-mediated programmed cell death by sphingosine-1-phosphate, Nature 1996, 800-803, 381.
Cuvillier et al., Sphingosine 1-phosphate inhibits activation of caspases that cleave poly(ADP-ribose) polymerase and lamins during Fas- and ceramide-mediated apopotosis in Jurkat T lymphocytes JBC 1998, 2910-2916, 273.
Cuvillier et al., Sphingosine 1-phosphate antagonizes apoptosis of human leukemia cells by inhibiting release cytochrome C and Smac/DIABLO from mitochondria, Blood 2001, 2828-2836, 98.
Cuvillier et al., Involvement of sphingosine in mitochondria-dependent Fas-induced apoptosis of Type II Jurkat T cells, JBC 2000, 15691-15700, 275.
Dai et al., Pharmacological inhibitors of the mitogen-activated protein kinase (MAPK) kinase/MAPK cascade interact synergistically with UCN-01 to induce mitochondrial dysfunction and apoptosis in human leukemia cells, Cancer Res 2001,5106-5115, 61.
De Jonghe et al., Structure-activity relationship of short chain sphingoid bases as inhibitors of sphingosine kinase, Bioorg Med Chem Lett 1999, 3175-3180, 9.
De Luca et al., NAD+/NADH as/or CoQ/CoQH2 ratios from plasma membrane electron transport may determine ceramide and sphingosine-1-phosphate levels accompanying G1 arrest and apoptosis, Biofactors 2005, 43-60, 25.
Edsall et al., N,N-dimethylsphingosine is a potent competitive inhibitor of sphingosine kinase but not of protein kinase C: modulation of cellular levels of sphingosine 1-phosphate and ceramide, Biochemistry 1998, 12892-12898, 37.
Filipits et al., Drug resistance factors in acute myeloid leukemia: a comparative analysis, Leukemia 2000, 68-76. 14.

(56) References Cited

OTHER PUBLICATIONS

French et al., Discovery and evaluation of inhibitors of human sphingosine kinase, Cancer Res 2003, 5962-5969, 63.
Gamble et al., Phenoxodiol, an experimental anticancer drug, shows potent antiangiogenic properties in addition to its antitumour effects, Int. J. Cancer 2006, 2412-2420, 118.
Hait et al., Sphingosine kinases, sphingosine 1-phosphate, apoptosis and diseases, Biochim Biophys Acta 2006, 2016-2026, 1758.
Hait et al., Role of sphingosine kinase 2 in cell migration toward epidermal growth factor, JBC 2005, 29462-29469, 280.
Hamada et al., Involvement of Mac-1-mediated adherence and sphingosine 1-phosphate in survival of phorbol ester-treated U937 cells, Biochem Biophys Res Commun 1998, 745-750, 244.
Igarashi et al., Effect of chemically well-defined sphingosine and its N-methyl derivatives on protein kinase C and src kinase activities, Biochemistry 1989, 6796-6800, 28.
Jarvis et al., Induction of apoptotic DNA damage and cell damage and cell death by activation of the sphingomyelin pathway, PNAS USA 1994, 73-77, 91.
Jarvis et al., Evidence for involvement of mitogen-activated protein kinase, rather than stress-activated protein kinase, in potentiation of 1-beta-D-arabinofuranosylcytosine-induced apoptosis by interruption of protein kinase c signaling, Mol Pharmacol 1998, 844-856, 54.
Jarvis et al., Coordinate regulation of stress- and mitogen-activated protein kinases in the apoptotic actions of ceramide and sphingosine, Mol Pharmacol 1997, 935-947, 52.
Jendiroba et al., Effective cytotoxicity against human leukemias and chemotherapy-resistant leukemia cell lines by N-N-dimethylsphingosine, Leuk Res. 2002, 301-310, 26.
Johnson et al., Intrinsic cytotoxicity and chemomodulatory actions of novel phenethylisothiocyanate sphingoid base derivatives in HL-60 human promyelocytic leukemia cells, J. Pharmacol. Exp. Therap. 2004, 452-461, 309.
Kim et al., Synthesis and evaluation of sphingoid analogs as inhibitors of sphingosine kinases, Bioorg & Med Chem 2005, 3475-3485, 13.
Kohama et al., Molecular cloning and functional characterization of murine sphingosine kinase, JBC 1998, 23722-23728, 273.
Kohno et al., Intracellular role for sphingosine kinase 1 in intestinal adenoma cell proliferation, Mol Cell Biol 2006, 7211-7223, 26.
Kono et al., F-12509A, a new sphingosine kinase inhibitor, produced by a discomycete, J. Antibiotics 2000, 459-466, 53.
Kono et al., B-5354 a, b, and c, new sphingosine kinase inhibitors, produced by a marine bacterium; taxonomy, fermentation, isolation, physico-chemical properties and structure determination, J. Antibiotics 2000, 753-758, 53.
Li et al., Sphingosine kinase-1 mediates BCR/ABL-induced upregulation of mcl-1 in chronic myeloid leukemia cells, Oncogene 2007, 7904-7908, 26.
Liu et al., Molecular cloning and functional characterization of a novel mammalian sphingosine kinase type 2 isoform, JBC 2000, 19513-19520, 275.
Maceyka et al., Sphk1 and Sphk2, sphingosine kinase isoenzymes with opposing functions in sphingolipid mechanism, JBC 2005, 37118-37129, 280.
Maggio et al., The histone deacetylase inhibitor MS-275 interacts synergistically with fludarabine to induce apoptosis in human leukemia cells, Cancer Res. 2004, 2590-2600, 64.
Marsolais & Rosen, Chemical modulators of sphingosine-1-phosphate receptors as barrier-oriented therapeutic molecules, Nature Reviews/Drug Discovery 2009, 297-307, 8.
McCormack et al, Animal models of acute myelogenous leukaemia-development, application and future perspectives, Leukemia 2005, 687-706, 19.
Milstien & Spiegel, Targeting sphingosine-1-phosphate: a novel avenue for cancer therapeutics, Cancer Cell 2006, 148-150, 9.
Mitra et al., Role of ABCC1 in export of sphingosine-1-phosphate from mast cells, PNAS USA 2006, 16394-16399, 103.
Moulding et al., Apoptosis is rapidly triggered by antisense depletion of mcl-1 in differentiating U937 cells, Blood 2000, 1756-1763, 96.
Neviani et al., FTY720, a new alternative for treating blast crisis chronic myelogenous leukemia and Philadelphia chromosome-positive acute lymphocytic leukemia, J Clin Invest 2007, 2408-2421, 117.
Ng et al., Marked suppression of tumor growth by FTY720 in a rat liver tumor model: the significance of down-regulation of cell survival Akt pathway, Int J Oncol 2007, 375-380, 30.
Niiro et al., (3z)-2-acetylamino-3-octadecen-1-ol as a potent apoptotic agent against HL-60 cells, Bioorg Med Chem 2004, 45-51, 12.
Nyakern et al., Frequent elevation of Akt kinase phosphorylation in blood marrow and peripheral blood mononuclear cells from high-risk myelodysplastic syndrome patients, Leukemia 2006, 230-238, 20.
Ogretman & Hannun, Biologically active sphingolipids in cancer pathogensis and treatment, Nature Rev Cancer 2004, 604-616, 4.
Okada et al., Involvement of N-terminal-extended form of sphingosine kinase 2 in serum dependent regulation of cell proliferation and apoptosis, JBC 2005, 36318-36325, 280.
Olivera et al., Sphingosine kinase expression increases intracellular sphingosine-1-phosphate and promotes cell growth and survival JBC 1999, 545-558, 147.
Paugh et al., The immunosuppressant FTY720 is phosphylated by sphingosine kinase type 2, FEBS lett 2003, 189-193, 554.
Pitson et al., Phosphorylation-dependent translocation of sphingosine kinase to the plasma membrane drives its oncogenic signalling, J Exp Med 2005, 49-54, 201.
Delgado et al., Inhibitors of sphingolipid metabolism enzymes, Biochimica et Biophysica Acta Biomembranes, 2006, 1957-1977, 1758.
Jeremias et al., Cell death induction by betulinic acid, ceramide and TRAIL in primary glioblastoma multiforme cells, Acta Neurochir (Wien), 2004, 721-729, 146.
Bektas et al., A sphingosine kinase inhibitor induces cell death in temozolomide resistant glioblastoma cells, Cancer Chemother Pharmacol 2009, 1053-1058, 64.
Van Brocklyn, James R., Sphingolipid signaling pathways as potential therapeutic targets in gliomas, Mini-Reviews in Medicinal Chemistry 2007, 984-990, 7.
Wong et al., Synthesis and Evaluation of Sphingosine Analogues as Inhibitors of Sphingosine Kinases, J. Med. Chem. 2009, 3618-3626, 52.
Rahmani et al., Coadministration of histone deacetylase inhibitors and perifosine synergistically induces apoptosis in human leukemia cells through Akt and ERK1/2 inactivation and the generation of ceramide and reactive oxygen species, Cancer Res 2005, 2422-2432, 65.
Rosato et al., The histone deacetylase inhibitor LAQ824 induces human leukocyte cell death through a process involving XIAP down-regulation, oxidative injury, and the acid sphingomyelinase-dependent generation of ceramide, Mol Pharmacol 2006, 216-225, 69.
Rosato et al., Mechanism and functional role of XIAP and Mcl-1 down-regulation in flavopiridol/vorinstat antileukemic interactions, Mol Cancer Ther 2007, 692-702, 6.
Sabbadini, R.A., Targeting sphingosine-1-phosphate for cancer therapy, Br J Cancer 2006, 1131-1135, 95.
Sobue et al., Quantitative RT-PCR analysis of sphingolipid metabolic enzymes in acute leukemia and myelodysplastic syndromes, Leukemia 2006, 2042-2046, 20.
Spiegel et al. Sphingosine-1-phosphate: an enigmatic signalling lipid, Nature Rev Mol Cell Biol. 2003, 397-407,4.
Steelman et al., JAK/STAT, Raf/MEK/ERK, P13/Akt and BCR-ABL in cell cycle progression and leukemogenesis Leukemia 2004, 189-218, 18.
Suguira et al., Ceramide kinase, a novel lipid kinase, JBC 2002, 23294-23300, 277.
Sukocheva et al. Estrogen transactivates EGFR via the sphingosine 1-phosphate receptor Edg-3: the role of sphingosine kinase-1, J Cell Biol 2006, 301-310, 173.

(56) References Cited

OTHER PUBLICATIONS

Sullards, et al., Analysis of sphingosine 1-phosphate, ceramides and other bioactive sphingolipids by high-performance liquid chromatography-tandem mass spectrometry, Science STKE 2001, L1.

Swanton et al., Regulators of mitotic arrest and ceramide metabolism are determinants of sensitivity of paclitaxel and other chemotherapeutic drugs, Cancer Cell 2007, 498-512, 11.

Taha et al., Loss of sphingosine kinase-1 activates the intrinsic pathway of programmed cell death: modulation of sphingolipid levels and the induction of apoptosis, FASEB J 2006, 482-484, 20.

XlA et al., Sphingosine kinase interacts with TRAF2 and dissects tumor necrosis factor-alpha signaling, JBC 2002, 7996-8003, 277.

Zhang et al., Bcl-2 interrupts the ceramide-mediated pathway of cell death, PNAS USA 1996, 5325-5328, 93.

U.S. Appl. No. 16/017,303, Rabbani et al.

Adamson et al., "Glioblastoma multiforme: a review of where we have been and where we are going," *Expert Opin. Investig. Drugs*, vol. 18, No. 8. pp. 1061-1083 (2009).

Bao et al., "Sphingosine kinase 1 promotes tumour cell migration and invasion via the S1P/EDG1 axis in hepatocellular carcinoma," *Liver International*, vol. 32, No. 2, pp. 331-338 (2012).

Beljanski et al., "Antitumor activity of sphingosine kinase 2 inhibitor ABC294640 and sorafenib in hepatocellular carcinoma xenografts," *Cancer Biology & Therapy*, vol. 11 No. 5 pp. 524-534 (2011).

Berge et al., "Pharmaceutical Salts," *Journal of Pharmaceutical Sciences*, vol. 66 No. 1, pp. 1-19 (1977).

Chandrasekhar et al., "Practical and highly stereoselective approaches to the total synthesis of (−)codonopsinine," *Tetrahedron: Asymmetry*, vol. 17 pp. 1380-1386 (2006).

Chen et al., "Relating hepatocellular carcinoma tumor samples and cell lines using gene expression data in translational research," *BMC Medical Genomics*, vol. 8, Suppl. 2, 10 pages (2015).

Cheng et al., "Ceramide production mediates cinobufotalin-induced growth inhibition and apoptosis in cultured hepatocellular carcinoma cells," *Tumor Biol.*, vol. 36, pp. 5763-5771 (2015).

Copending U.S. Appl. No, 16/017,303—Non-Final Office Action dated Sep. 5, 2018, 12 pages.

Freeman (ed.), "Cancer Principles & Practice of Oncology", $6^{th}$ Ed., Lippincott Williams & Wilkins (Philadelphia, PA) pp. 2119-2120 (2001).

French et al., "Pharmacology and Antitumor Activity of ABC294640, a Selective Inhibitor of Sphingosine Kinase-2," *The Journal of Pharmacology and Experimental Therapeutics*, vol. 333, No. 1, pp. 129-139 (2010).

Gokel et al., *Israel J. Chem.*, (CAPLUS Abstract), vol. 32, pp. 127-133 (1992).

Guo et al., A Prototype Intelligent Hybrid System for Hard Gelatin Capsule Formulation Development, *Pharmaceutical Technology*, pp. 44-60 (2002).

Gura et al., *Science*, vol. 278, pp. 1041-1042 (1997).

International Search Report for priority application PCT/US2010/32939 (2 pages).

Johnson et al., *British Journal of Cancer*, vol. 84 pp. 1424-1431 (2001).

Kapitonov et al., "Targeting Sphingosine Kinase 1 inhibits Akt Signaling, Induces Apoptosis, and Suppresses Growth of Human Glioblastoma Cells and Xenografts," *Cancer Research*, vol. 69, No. 17, pp. 6915-6923 (2009).

Karuppuchamy et al., "Sphingosine-1-phosphate receptor-1 (S1P1) is expressed by lymphocytes, dendritic cells, and endothelium and modulated during inflammatory bowel disease." *Nature*, vol. 10, No. 1, pp. 162-171 (2017).

Kawamori et al., "Sphingosine kinase 1 is up-regulated in colon carcinogenesis," *The FASEB Journal*, vol. 20, No. 2, p. 386-388 (2018).

Kim et al., "Sphingosine 1-phosphate (S1P) induces shape change in rat C6 gloma cells through the S1P2 receptor: development of an agonist for S1P receptors," *J. Pharma. Pharmacol.*, vol. 59, pp. 1035-1041 (2007).

Kim et al., "synthesis and Cytotoxicity of New Aromatic Ceramide Analogs with Alkylsulfonamido Chains,"*Arch. Pharm. Res.*, vol. 30, No. 5, pp. 570-580 (2007).

Kunkel et al., "Targeting the sphingosine-1-phosphate axis in cancer, inflammation and beyond," *Nature*, vol. 12, pp. 688-702 (2013).

Li et al., "A novel sphingosine knase 1 inhibitor (SKI-5C) induces cell death of Wilms' tumor cells in vitro and in vivo," *Am J Transl Res*, vol. 8, No. 11, pp. 4548-4563 (2016).

Liang et al, "Sphingosine-1-Phosphate Links Persistent STAT3 Activation, Chronic Intestinal Inflammation, and Development of Colitis-Associated Cancer," *Cancer Cell*, vol. 23, No. 1, pp. 107-120 (2013).

Lim et al., "Syntheses of sphingosine-1-phosphate analogues and their interaction EDG/SIP receptors," *Bioorganic & Medicinal Chemistry Letters*, vol. 14, pp. 2499-2503 (2004).

Liu et al., "SPHK1 (sphingosine kinase 1) induces epithelial-mesenchymal transition by promoting the autophagy-linked lysosomal degradation of CDG1/E-cadherin in hepatoma cells,"*Autophagy*, vol. 13, No. 5, pp. 900-913 (2017).

Lu et al., "Identification of sphingosine kinase 1 (SphK1) as a primary target of incaritin in hepatocellular carcinoma cells," *Oncotarget* vol. 8, No. 14, pp. 22800-22810 (2017).

Lu et al., Long non-coding RNA HULC promotes tumor angiogenesis in liver cancer by up-regulating sphingosine kinase 1 (SPHK1), *Oncotarget*, vol. 7, No. 1, pp. 241-254 (2015).

Maines et al., "Suppression of Ulcerative Colitis in Mice by Orally Available Inhibitors of Sphingosine Kinase," *Dig Dis Sci*, vol. 53, pp. 997-1012 (2008).

Mulzer et al., *Chem. Berichte* (CAPLUS Abstract), vol. 114, pp. 37-1-24 (1981).

Murakami et al., "Efficient sterodivergent synthesis of erythro- and threo-sphingosines: unprecedented reversal of the stereochemistry in the addition," *Tetrahedron*, vol. 58, pp. 9257-9263 (2002).

Murakami et al., "Synthesis and biological properties of novel sphingosine derivatives,", *Bioorganic & Medicinal Chemistry Letters*, vol. 15, pp. 1115-1119 (2005).

Neidle (Ed.), "Cancer Drug Design and Discovery," Academic Press, pp. 427-431 (2008).

Overmeire et al., "Synthesis and biological Evaluation of Ceramide Analogues with Substituted Aromatic Rings or an Allylic Fluoride in the Sphingoid Moiety,"*J. Med. Chem.*, vol. 43, pp. 4189-4199 (2000).

Paugh et al., "A selective sphingosine kinase 1 inhibitor integrates multiple molecular therapeutic targets in human leukemia," *Blood*, vol. 112, p. 1382-1391 (2008).

PCT/US2018/039263—Annex to Form PCT/ISA/206, Communication Relating to the Results of the Partial International Search (2018).

Peyrin-Biroulet et al., "Modulation of sphingosine-1-phosphate in inflammatory bowel disease," *Autoimmunity Reviews*, vol. 16, p. 495-503 (2017).

Pitman et al., "Recent advances in the development of sphingosine kinase inhibitors," *Cellular Signalling*, vol. 28, pp. 1340-1363 (2016).

Pyne et al., " Sphigosine 1-Phosphate is a Missing Link between Chronic Inflammation and Colon Cancer," *Cancer Cell*, vol. 23, pp. 5-7 (2013).

Rex et al., "Sphingosine Kinase Activity is not Required or Tumor Cell Viability," *PLOSone*, vol. 8, Issue 7, pp. e68328-e68328 (2013).

Sausville et al., "Contributions of Human Tumor Xenografts to Anticancer Drug Development," *Cancer Res.*, vol. 66, No. 7, pp. 3351-3354 (2006).

Schnute et al., "Modulation of cellular S1P levels with a novel, potent and specific inhibitor of sphingosine kinase-1," *Biochem J.*, vol. 44, pp. 79-88 (2012).

Scott et al., "Ozanimod (RPC1063) is a potent sphingosine-1-phosphate receptor-1 (S1P1) and receptor-5 (S1P5) agonist with autoimmune disease-modifying activity," *British Journal of Pharmacology*, vol. 173, pp. 1778-1792 (2016).

Warunis et al., Berichte der Deutschen Chemischen Gesellscaft (CAPLUS Abstract), vol. 43, pp. 654-660 (1910).

(56) References Cited

OTHER PUBLICATIONS

Wolk et al, "The Incidence of Central Nervous System Leukemia in Adults with Acute Leukemia," *Cancer*, vol. 33, pp. 863-869 (1974).
Zeng et al., "Sphingosine-1-phosphate induced epithelial-mesenchymal transition of hepatocellular carcinoma via an MMP-7/syndecan-1/TGB-β autocrine loop," *Oncotarget*, vol. 7, No. 39, pp. 63324-63337 (2016).
Karuppuchamy et al., "Sphingosine-1 phosphate receptor-1 (S1P(1)) is expressed by lymphocytes, dendritic cells and edothelium and modulated during inflammatory bowel disease," *Mucosal Immunology*, vol. 10, No. 1, pp. 162-171 (2017).
Long et al., "Ceramide production mediates cinobufotalin-induced growth inhibition and apoptosis in cultured helpatocellular carcinoma cells," *Tumor Biology*, vol. 36, No. 8, pp. 5763-5571 (2015)—Abstract Only.
Lu et al., "Identification of sphingosine kinase 1 (SphK1) as a primary target of icaritin in hepatocellular carcinoma cells," *Oncotarget*, vol. 8, No. 14, pp. 22800-22810 (2017).
Peyrin-Biroulet et al., "Modulation of sphingosine-1-phosphate in inflammatory bowel disease," *Autoimmunity Reviews*, vol. 16, No. 5, pp. 495-503 (2017).
Pitman et al., "Recent advances in the development of sphingosine kinase inhibitors," *Cellular Signalling*, vol. 28, No. 9, pp. 1349-1363 (2016).

\* cited by examiner

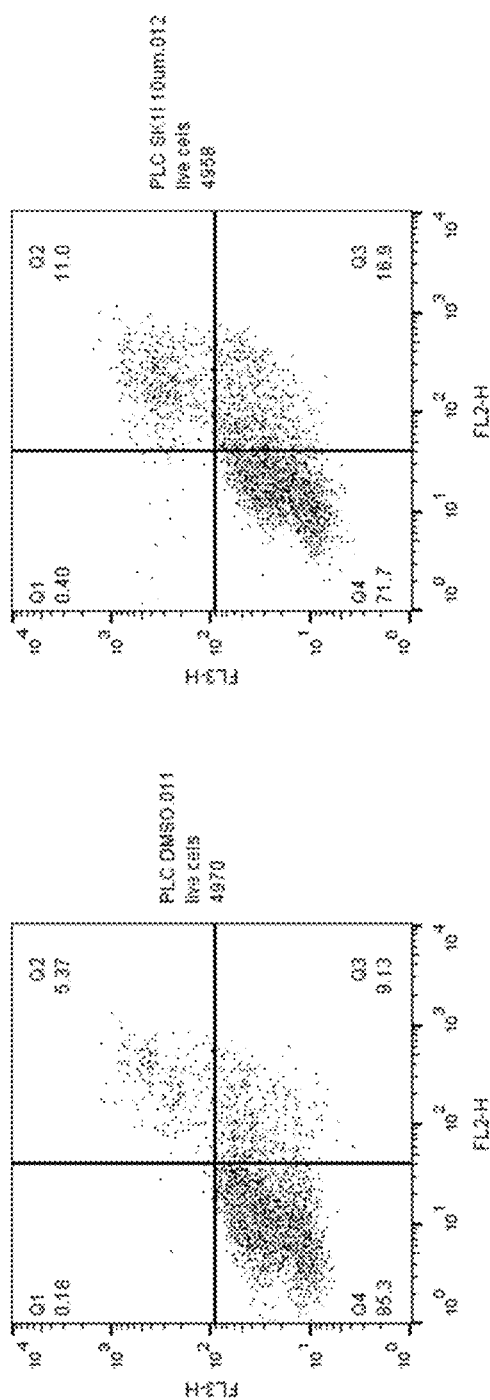
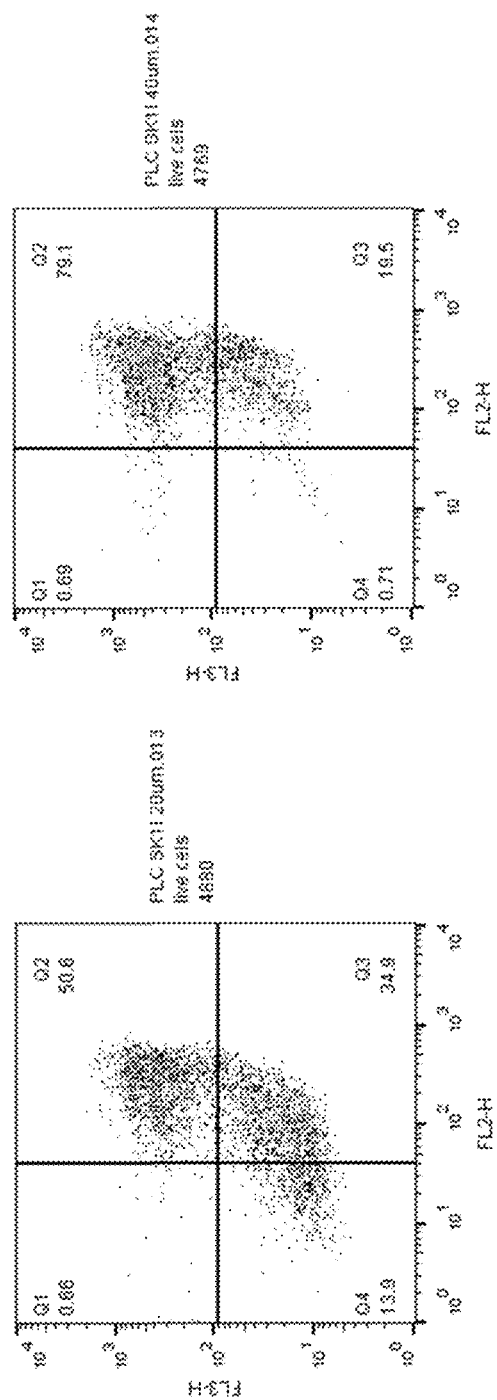
FIG. 6A  FIG. 6B  FIG. 6C  FIG. 6D

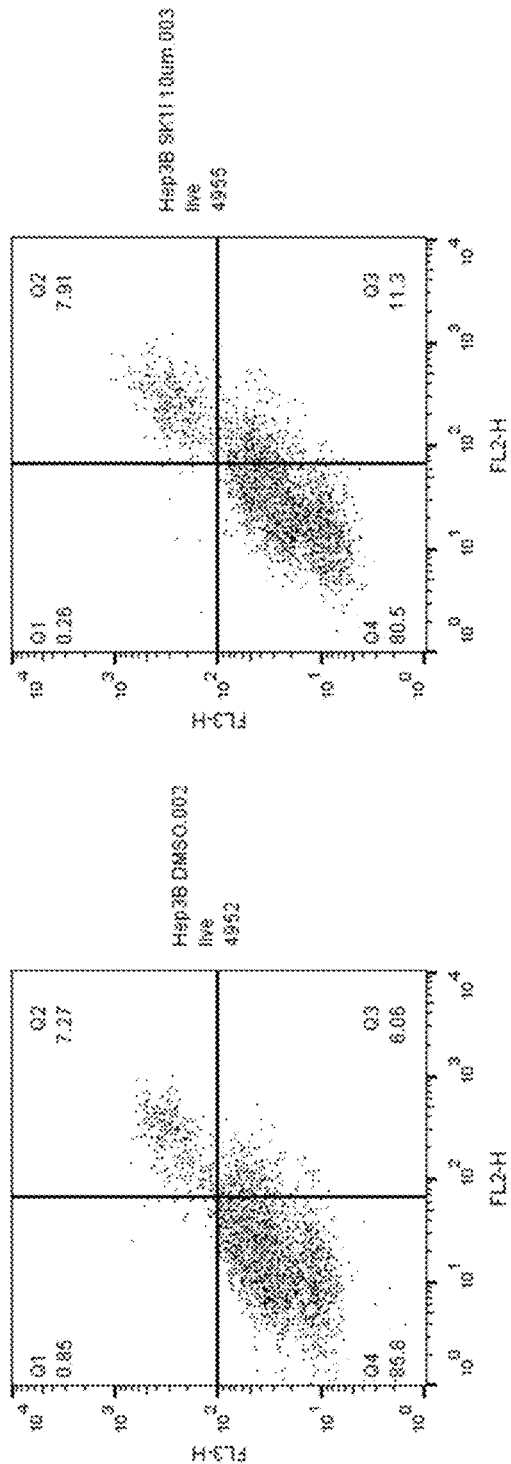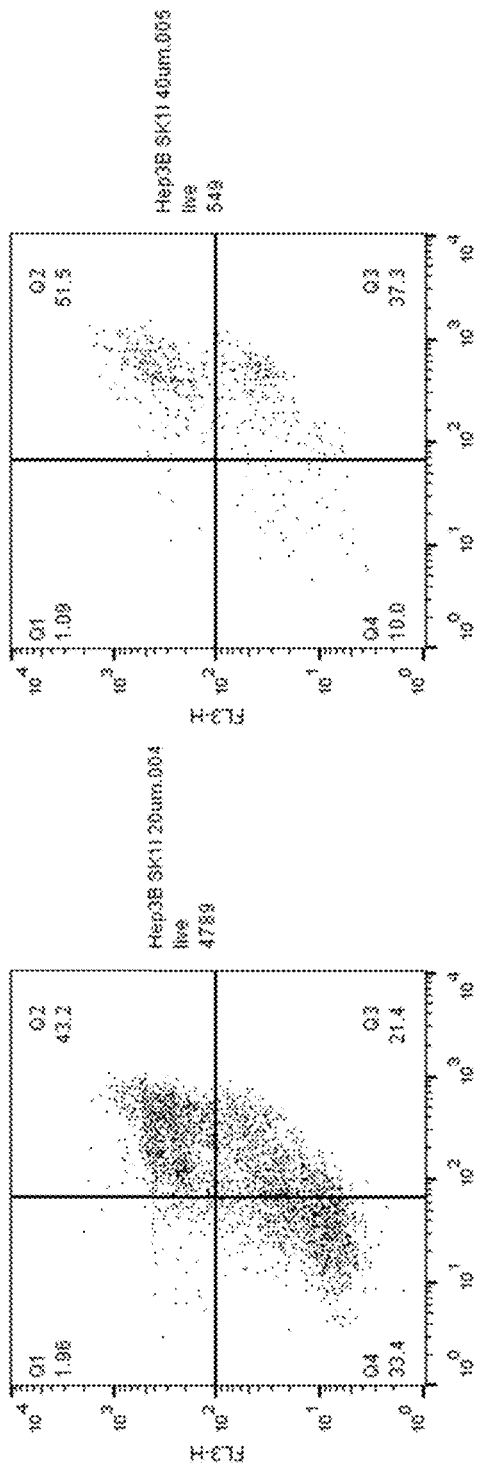
FIG. 7A  FIG. 7B  FIG. 7C  FIG. 7D

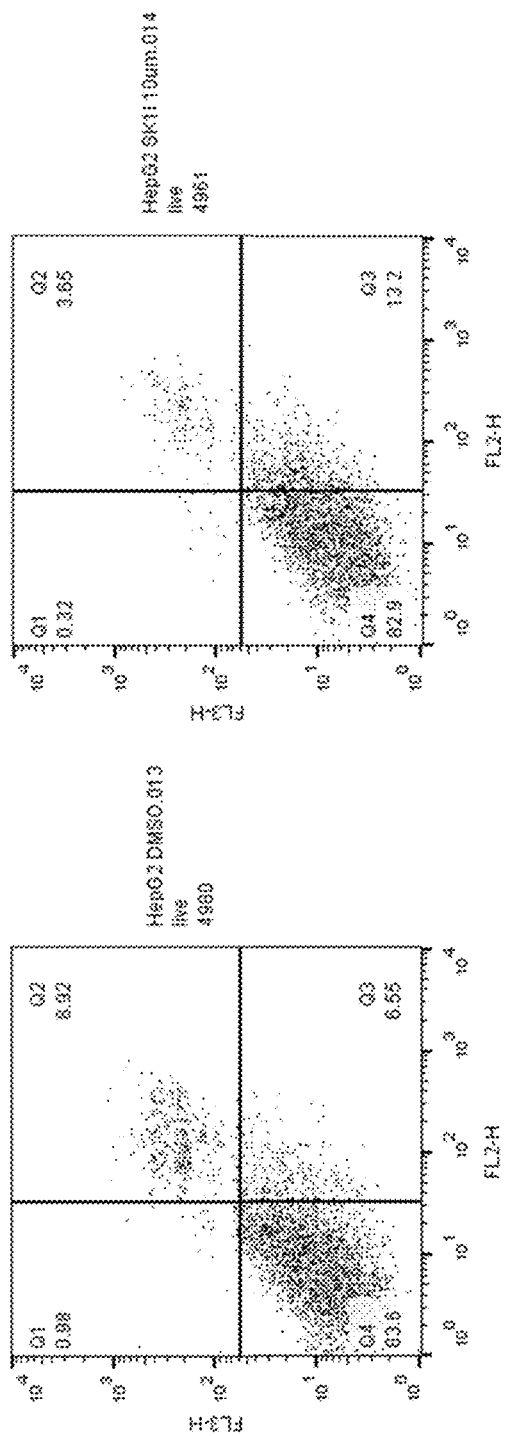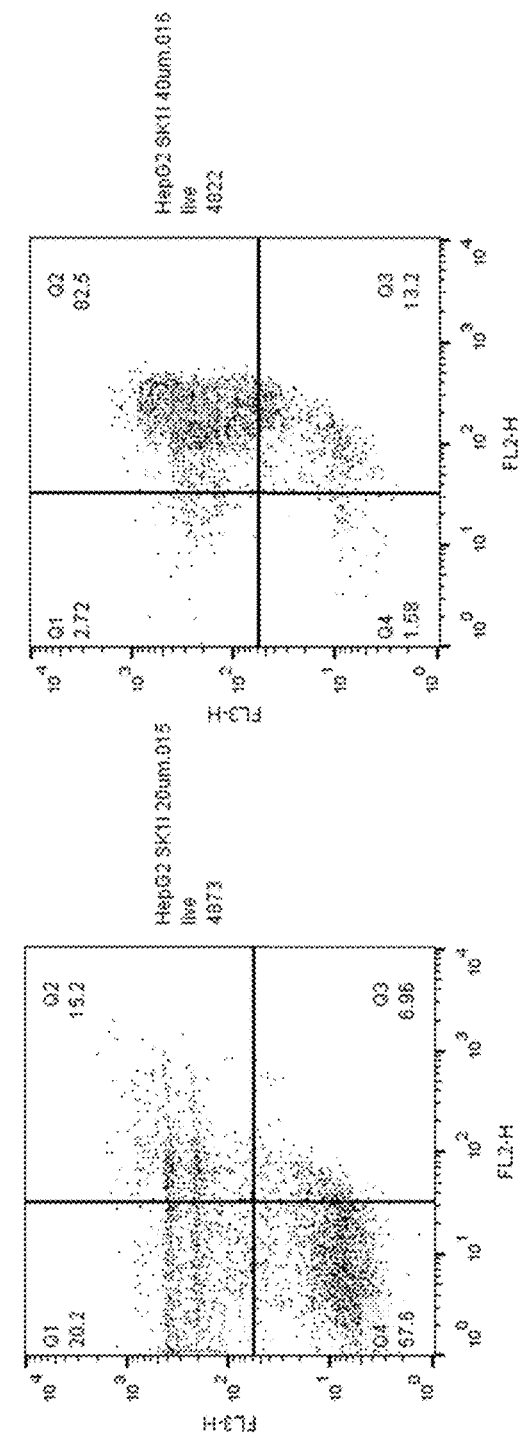
FIG. 8A  FIG. 8B  FIG. 8C  FIG. 8D

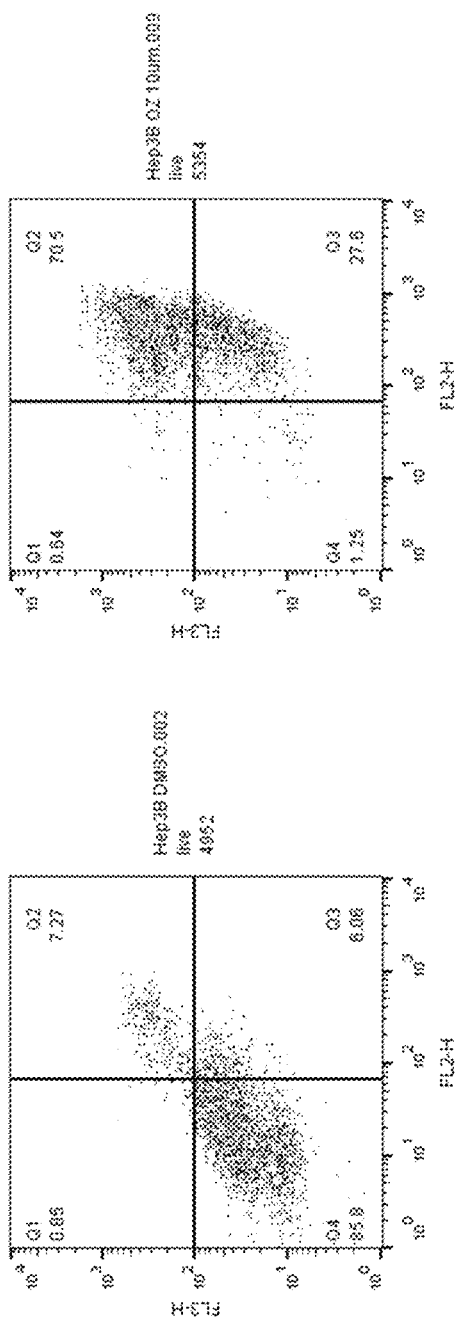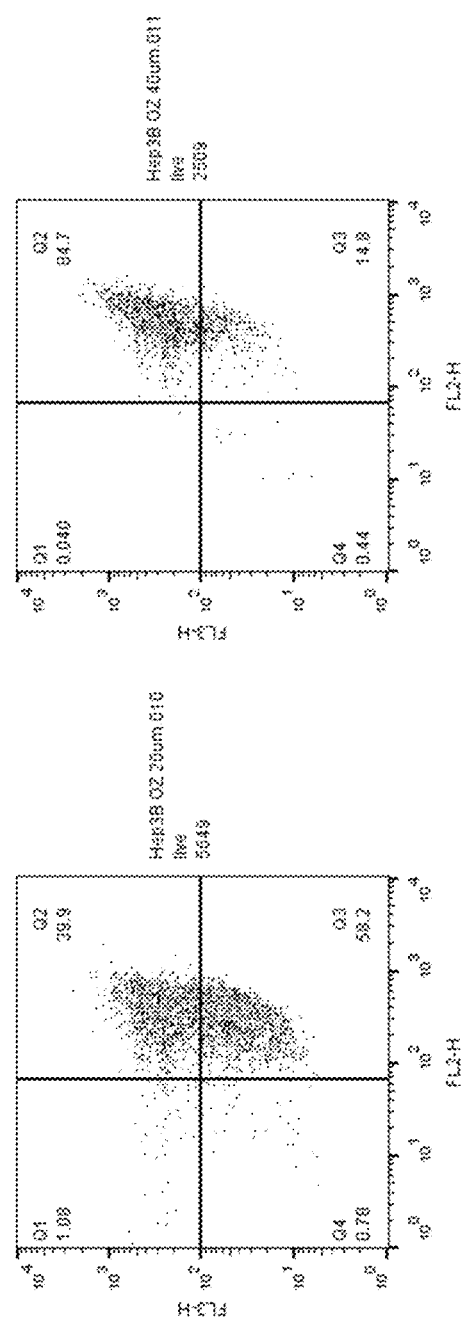
FIG. 11A  FIG. 11B  FIG. 11C  FIG. 11D

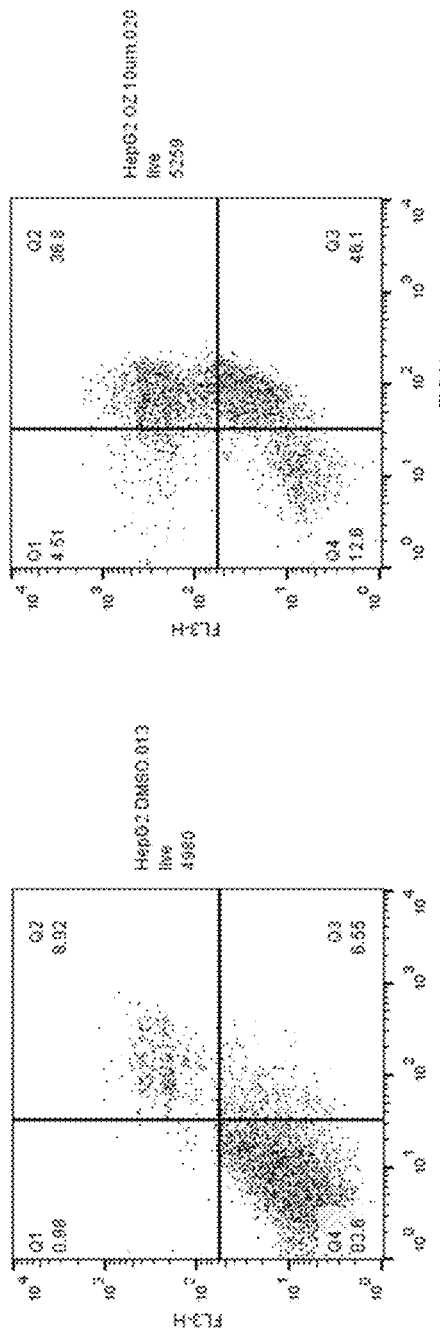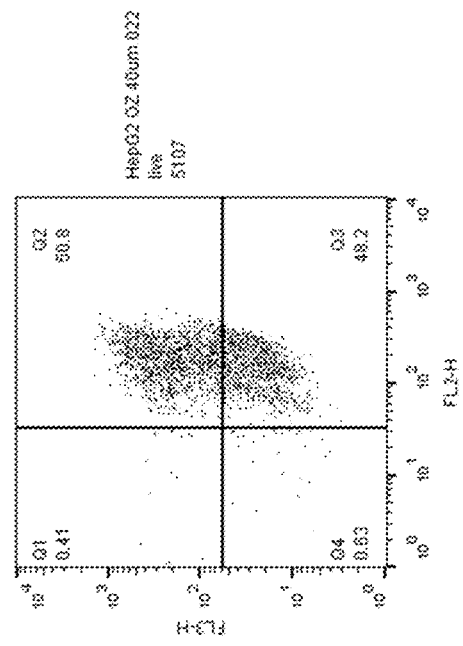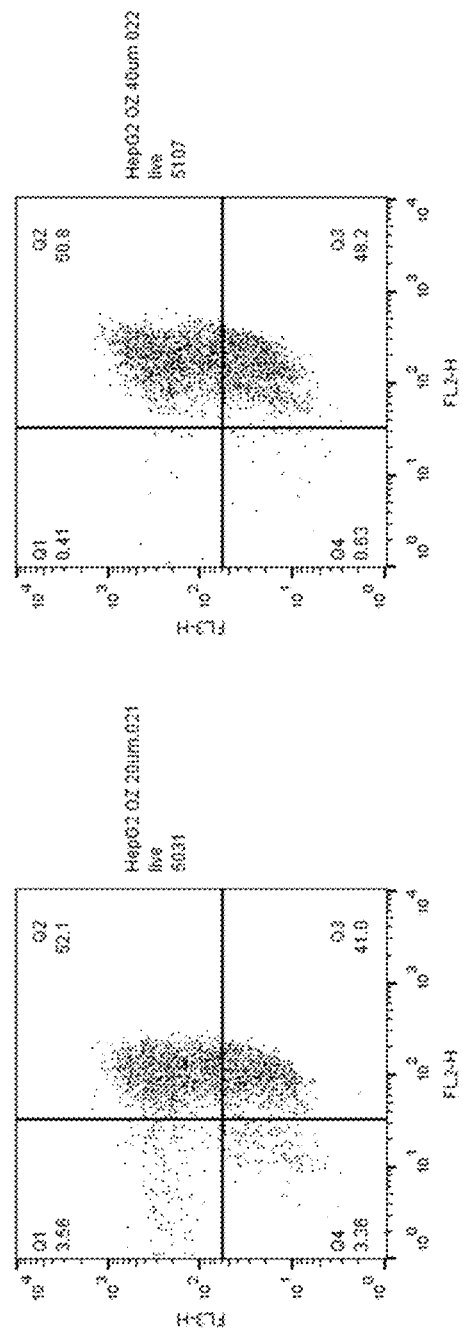
FIG. 12A
FIG. 12B
FIG. 12C
FIG. 12D

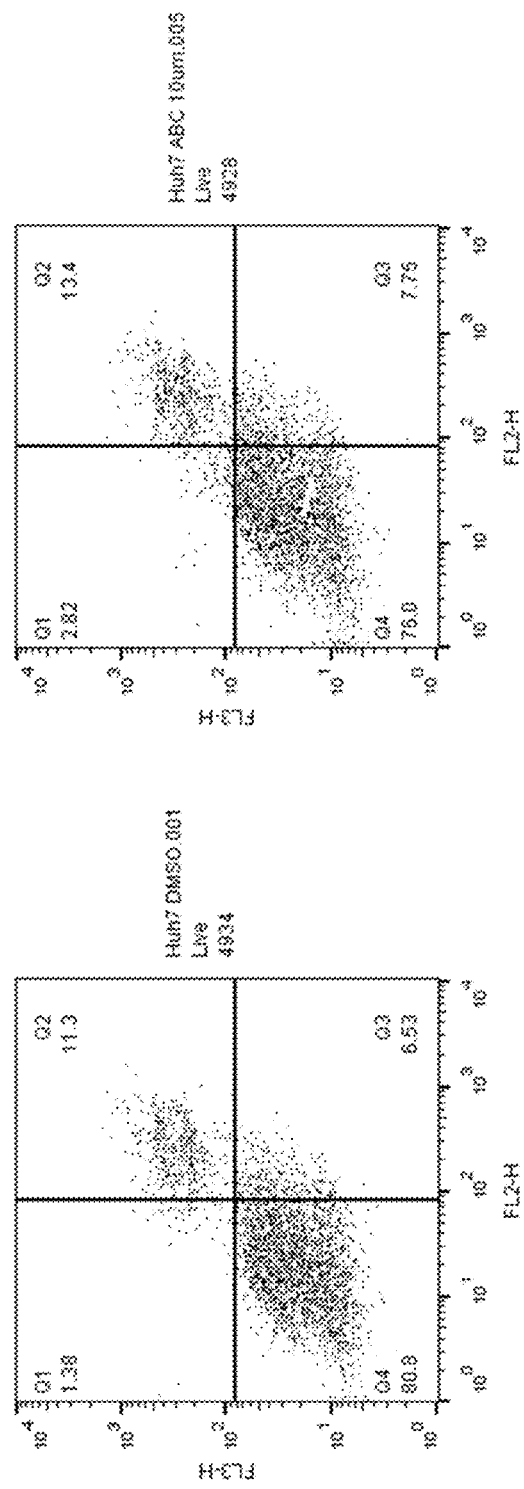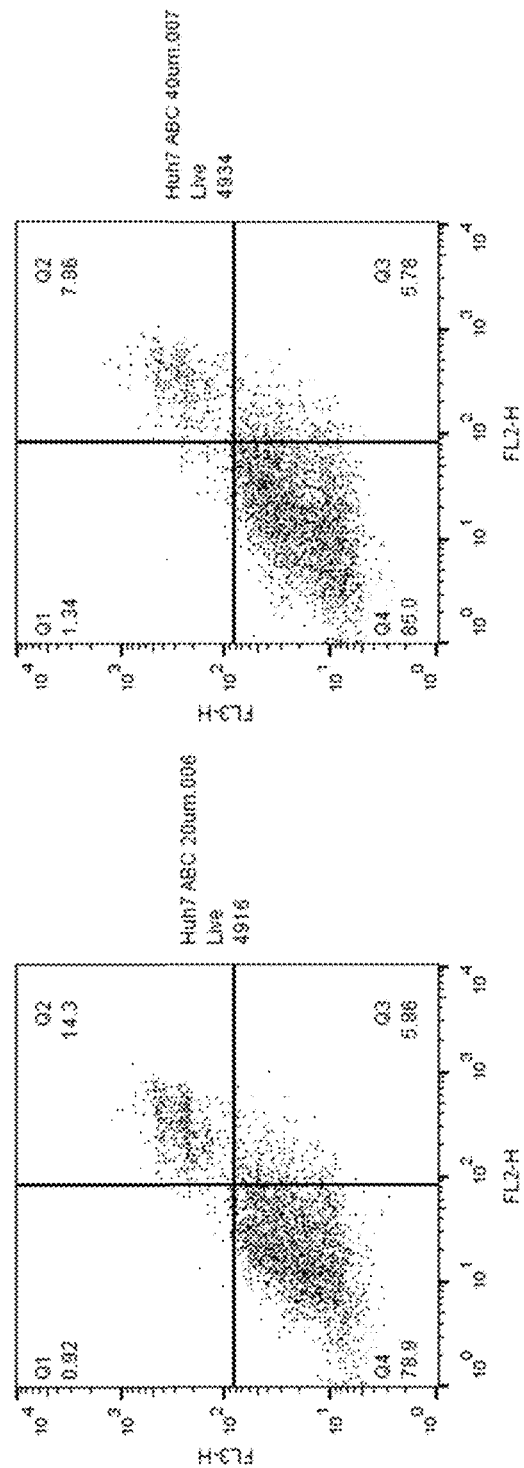

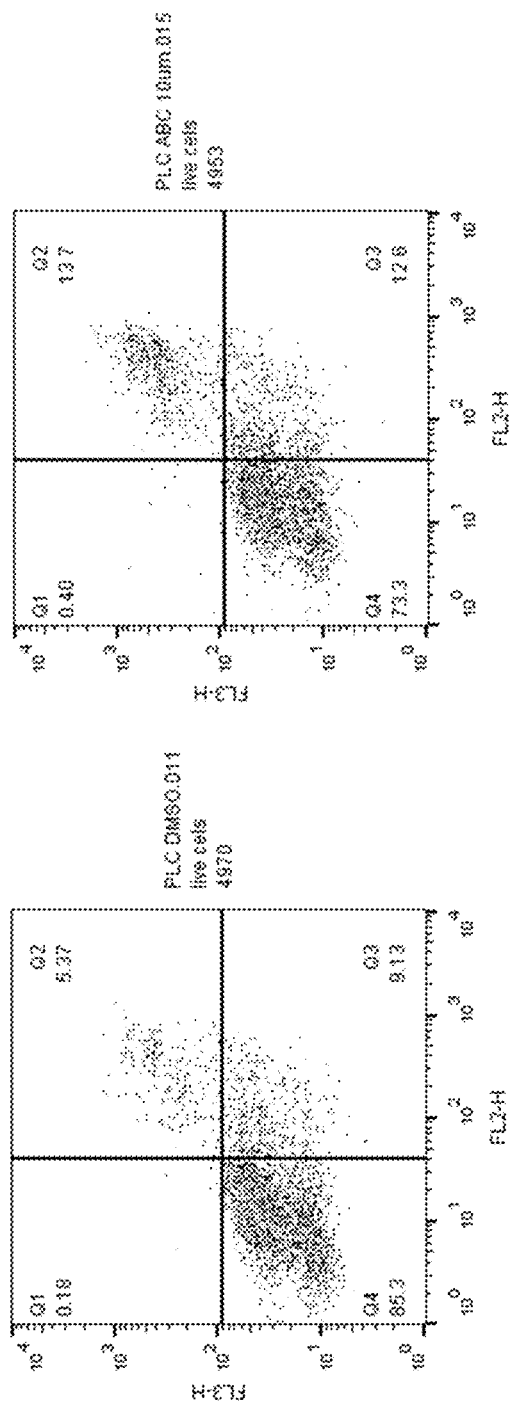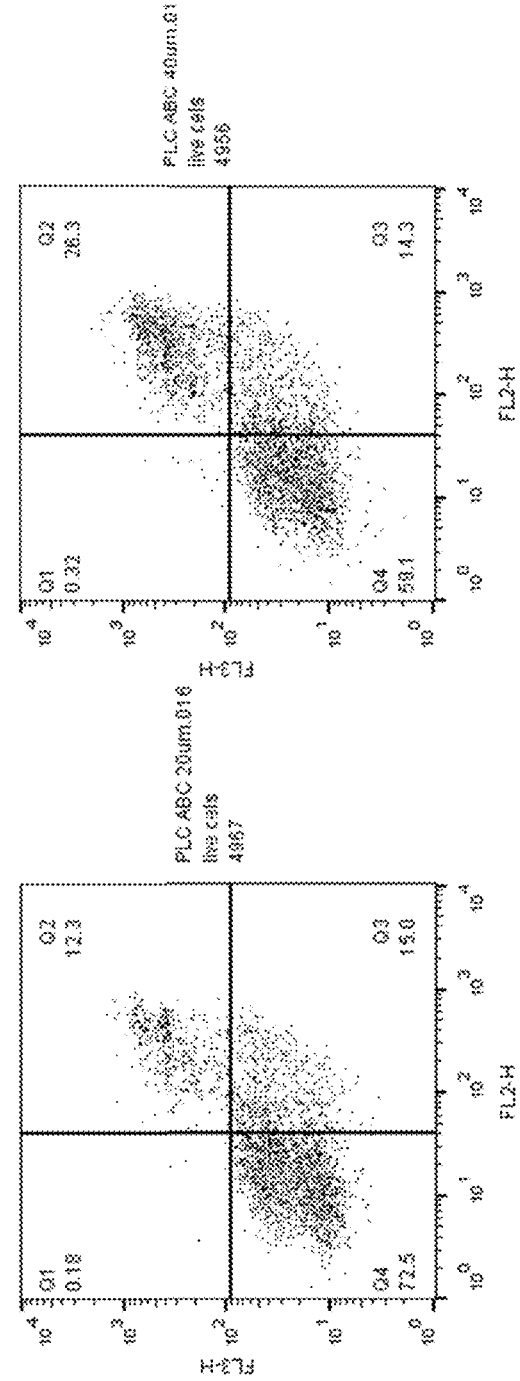
FIG. 14A
FIG. 14B
FIG. 14C
FIG. 14D

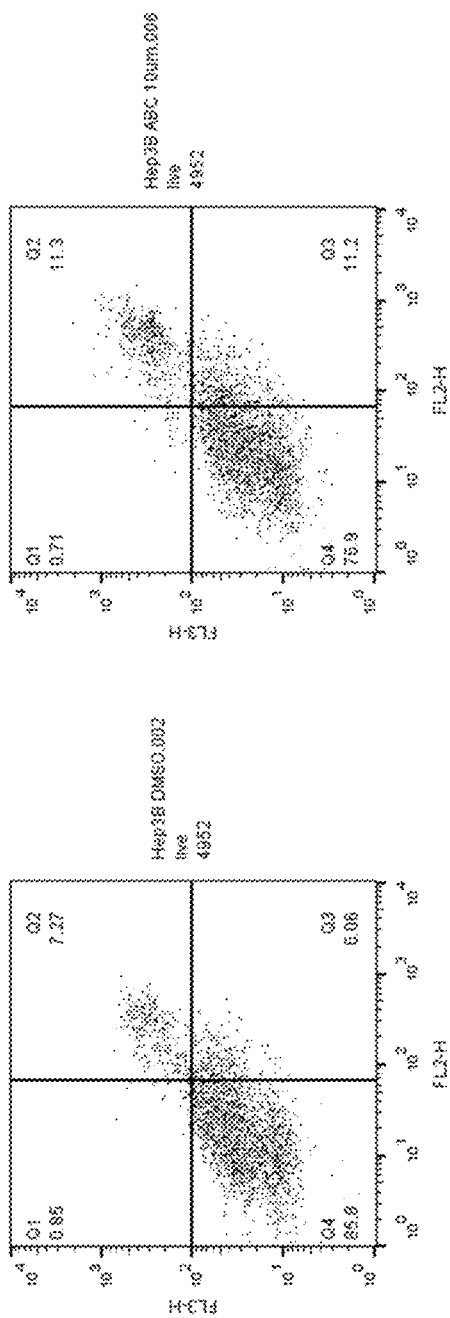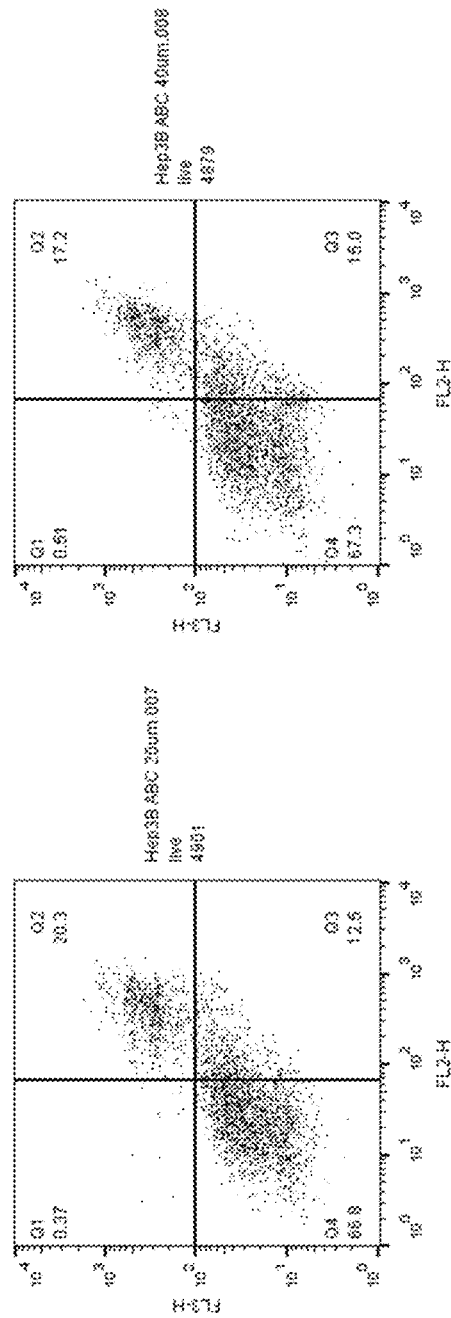
FIG. 15A  FIG. 15B  FIG. 15C  FIG. 15D

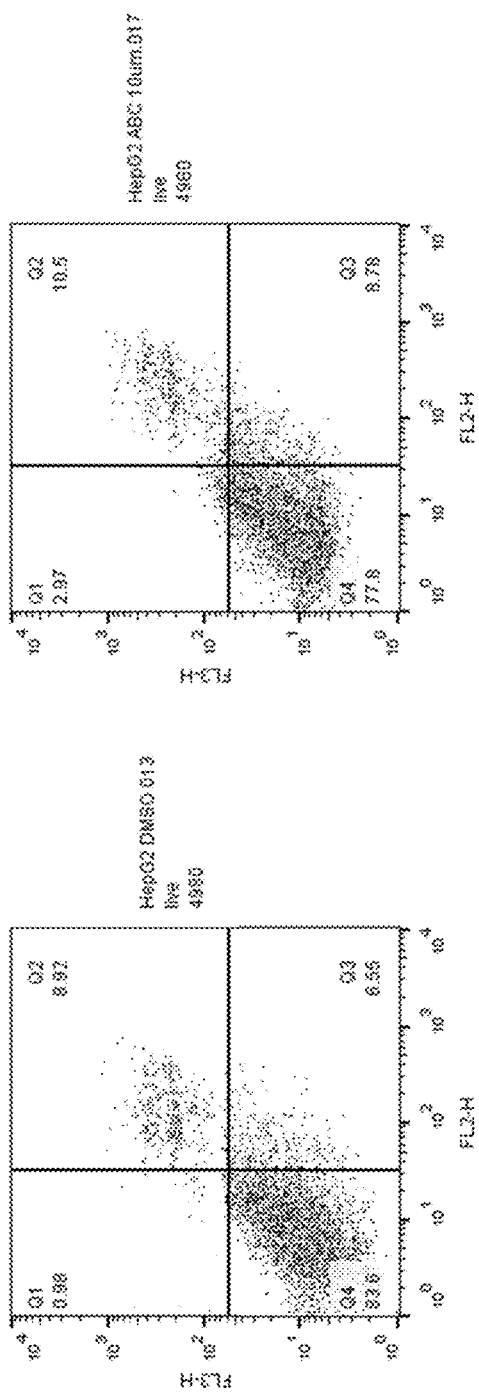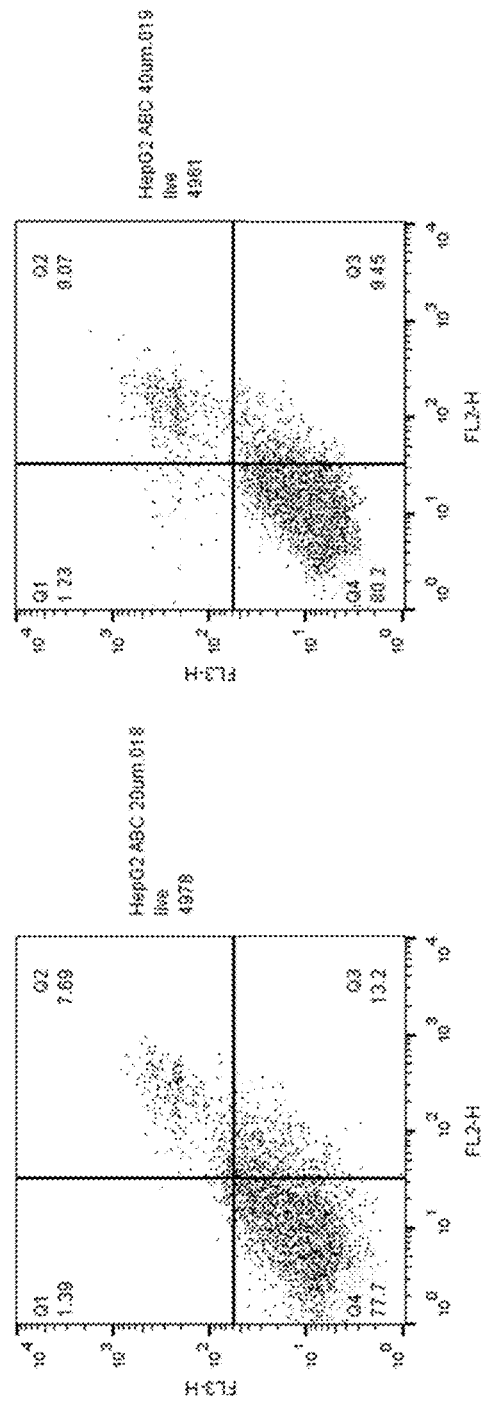
FIG. 16A  FIG. 16B  FIG. 16C  FIG. 16D

SPHINGOSINE PATHWAY MODULATING COMPOUNDS FOR THE TREATMENT OF CANCERS

CROSS-REFERENCE TO RELATED APPLICATIONS

This application is a divisional of U.S. patent application Ser. No. 16/017,345 filed Jun. 25, 2018, which claims the benefit of U.S. provisional patent application Ser. No. 62/524,221 filed Jun. 23, 2017, each of which is hereby incorporated by reference in its entirety.

FIELD OF THE INVENTION

The invention relates to the field of pharmaceutical treatment of cancers.

BACKGROUND

Sphingosine-1-phosphate (S1P) was discovered to be a bioactive signaling molecule over 20 years ago. Studies have since identified two related kinases, sphingosine kinase 1 and 2 (a/k/a sphingosine kinase "type I" and "type II" respectively, and SphK1 and SphK2 respectively), which catalyze the phosphorylation of sphingosine to S1P. Extracellular S1P can bind to and activate each of five S1P-specific, G protein-coupled receptors (designated $S1PR_{1-5}$) to regulate cellular and physiological processes in an autocrine or paracrine manner. Selective inhibitors of each of sphingosine kinase 1 and 2, as well as both non-selective and selective agonists of S1PRs, have been developed and are known in the art.

SUMMARY

One embodiment of the invention provides a method for treating liver cancer, such as hepatocellular carcinoma (HCC), in a mammalian subject, such as a human, that includes the step of:

administering to a mammalian subject in need of treatment for liver cancer, a therapeutically effective amount of a sphingosine kinase type I inhibitor, such as SK1-I or a pharmaceutically acceptable salt thereof.

A related embodiment of the invention provides a pharmaceutical composition that includes a sphingosine kinase type I inhibitor, such as SK1-I or a pharmaceutically acceptable salt thereof for the treatment of liver cancer, such as HCC, in a mammal, such as a human patient.

Another embodiment of the invention provides a method for treating a cancer or a myeloproliferative disorder (myeloproliferative neoplasm) in a mammalian subject, such as a human, that includes the step of:

administering to a mammalian subject in need of treatment for a cancer or myeloproliferative disorder, a therapeutically effective amount of a sphingosine-1-phosphate receptor agonist, such as an agonist of one or both of sphingosine-1-phosphate receptor-1 ($S1P_1$) and sphingosine-1-phosphate receptor-5 ($S1P_5$) such as ozanimod (RPC1063) or a pharmaceutically acceptable salt thereof.

A related embodiment of the invention provides a pharmaceutical composition for the treatment of a cancer or a myeloproliferative disorder (myeloproliferative neoplasm) in a mammalian subject, such as a human, that includes:

a therapeutically effective amount of a sphingosine-1-phosphate receptor agonist, such as an agonist of one or both of sphingosine-1-phosphate receptor-1 ($S1P_1$) and sphingosine-1-phosphate receptor-5 ($S1P_5$) such as ozanimod (RPC1063) or a pharmaceutically acceptable salt thereof.

Still another embodiment of the invention provides a method for treating a cancer or a myeloproliferative disorder (myeloproliferative neoplasm), such as any of those disclosed herein, in a mammalian subject, such as a human, including the step of:

co-administering to a mammalian subject in need of treatment for a cancer or myeloproliferative disorder, a therapeutically effective amount of:

(a) a sphingosine kinase type I inhibitor, such as one disclosed in U.S. Pat. Nos. 8,372,888 and/or 8,314,151, such as SK1-I, or a pharmaceutically acceptable salt thereof; and (b) one or more immune checkpoint inhibitors, which may be monoclonal antibodies, such as one or more selected from the group consisting of: PD-1 inhibitors such as mAbs Pembrolizumab (Keytruda®) and Nivolumab (Opdivo®); PD-L1 inhibitors such as mAbs Atezolizumab (Tecentriq®), Avelumab (Bavencio®), and Durvalumab (Imfinzi®); and CTLA-4 inhibitors such as mAb Ipilimumab (Yervoy®); and V-domain Ig Suppressor of T Cell Activation (VISTA) inhibitors such as mAb JNJ-61610588 (ImmuNext Inc.).

Additional features, advantages, and embodiments of the invention may be set forth or apparent from consideration of the following detailed description, drawings if any, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

FIGS. 6A-D show apoptosis assay data for various concentrations of SK1-I and no-drug control for PLC-PRF5 cells. SK1-I strongly induced apoptosis in the PLC-PRF5 cells.

FIGS. 7A-D show apoptosis assay data for various concentrations of SK1-I and no-drug control for Hep 3B cells. SK1-I strongly induced apoptosis in the Hep 3B cells.

FIGS. 8A-D show apoptosis assay data for various concentrations of SK1-I and no-drug control for Hep G2 cells. SK1-I strongly induced apoptosis in the Hep G2 cells.

FIGS. 11A-D show apoptosis assay data for various concentrations of ozanimod and no-drug control for Hep 3B cells. Ozanimod strongly induced apoptosis in the Hep 3B cells.

FIGS. 12A-D show apoptosis assay data for various concentrations of ozanimod and no-drug control for Hep G2 cells. Ozanimod strongly induced apoptosis in the Hep G2 cells.

FIGS. 13A-D shows apoptosis assay data for various concentrations of ABC294640 and no-drug control for Huh7 cells. ABC294640 failed to induce apoptosis in the Huh7 cells.

FIGS. 14A-D show apoptosis assay data for various concentrations of ABC294640 and no-drug control for PLC-PRF5 cells. ABC294640 did not substantially induce apoptosis in the PLC-PRF5 cells.

FIGS. 15A-D show apoptosis assay data for various concentrations of ABC294640 and no-drug control for Hep 3B cells. ABC294640 did not substantially induce apoptosis in the Hep 3B cells.

FIGS. 16A-D show apoptosis assay data for various concentrations of ABC294640 and no-drug control for Hep G2 cells. ABC294640 failed to induce apoptosis in the Hep G2 cells.

DETAILED DESCRIPTION

Figure 1:
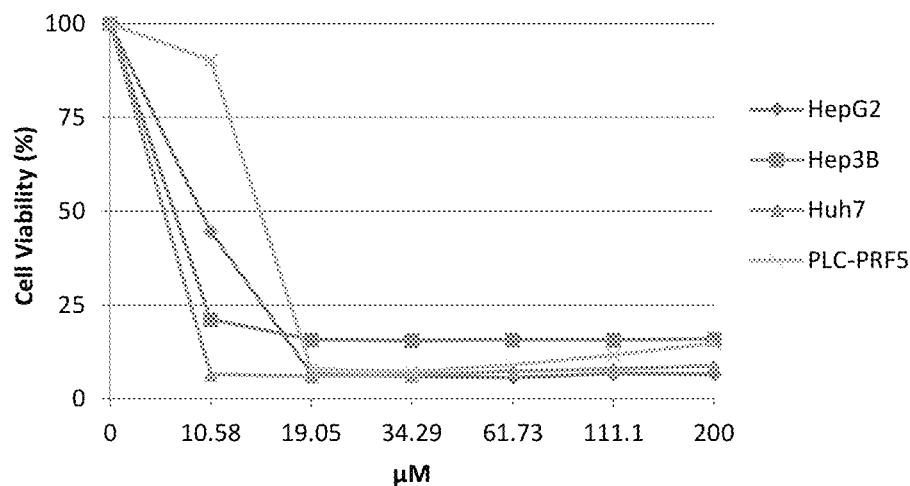
FIG. 1 shows MTT assay data (72 hours) for various concentrations of ozanimod for four human hepatocellular carcinoma cell lines.

The invention provides new uses of sphingosine kinase-1 inhibitors, such as SK1-I, and selective sphingosine-1-phosphate receptor agonists, such as ozanimod, for treating cancers, such as a liver cancer, and myeloproliferative neoplasms (myeloproliferative disorders), in mammals, such as human patients. The invention also provides new uses of selective sphingosine kinase type I inhibitors, such as SK1-I, and selective sphingosine-1-phosphate receptor agonists, such as ozanimod, for inducing apoptosis and/or necrosis of mammalian, such as human, cancer cells, such as liver cancer cells, and myeloproliferative neoplasm cells.

Sphingosine kinase 1 inhibitors used in various embodiments of the invention may, for example, include any of those disclosed in U.S. Pat. Nos. 8,372,888 and/or 8,314,151, each of which is hereby incorporated by reference in its entirety herein, or pharmaceutically acceptable salts thereof. The sphingosine kinase I inhibitor may, for example, be (E,2R,3S)-2-(methylamino)-5-(4-pentylphenyl)pent-4-ene-1,3-diol (also known as SK1-I), or a pharmaceutically acceptable salt thereof such as but not limited to a hydrochloride salt. The structure of SK1-I is shown below.

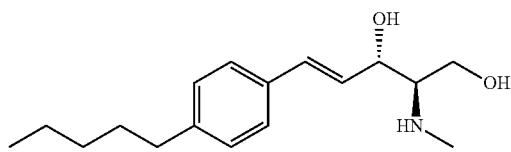 [SMILES: CCCCCc1ccc(/C=C/[C@H](O)[C@@H](CO)NC)cc1]

See also Paugh et al., Blood, 2008 112: 1382-1391.

The sphingosine kinase I inhibitor may, for example, be a compound having the structure

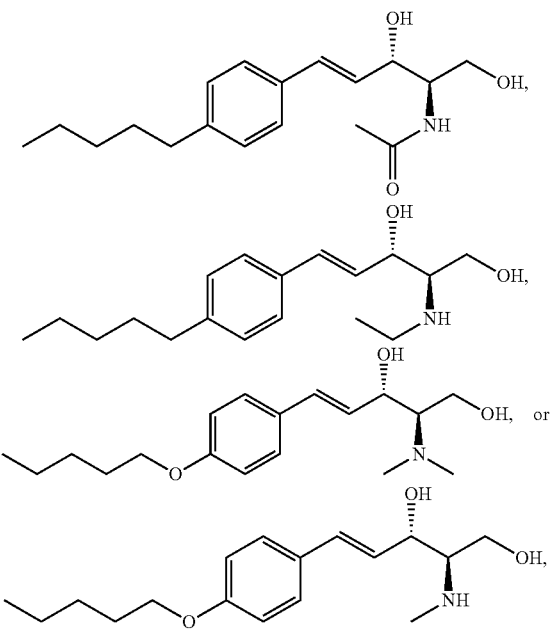

or a pharmaceutically acceptable salt of the compound such as but not limited to a hydrochloride salt.

The sphingosine kinase I inhibitor may, for example, be a compound having the structure

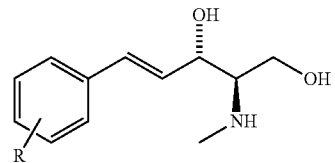

wherein R is selected from a straight carbon chain, a branched carbon chain, a straight carbon chain comprising one or more heteroatoms, a branched carbon chain comprising one or more heteroatoms, a cyclic ring, a heterocyclic ring, an aromatic ring, a hetero-aromatic ring, or any combination of the foregoing, or a pharmaceutically acceptable salt thereof such as but not limited to a hydrochloride salt.

The sphingosine kinase I inhibitor may, for example, be a compound having the structure

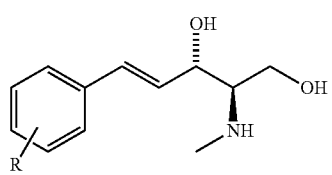

wherein R is 3,4-dimethoxy, 4-phenyl or 3-pentyl, or a pharmaceutically acceptable salt thereof such as but not limited to a hydrochloride salt.

Sphingosine-1-phosphate receptor agonists used in various embodiments of the invention may, for example, be any of those disclosed in any of U.S. Pub. Nos. 20110172202, 20130231326, and 20150299149, or pharmaceutically acceptable salts thereof. The agonists may be agonists of one or both of sphingosine-1-phosphate receptor-1 ($S1P_1$) and sphingosine-1-phosphate receptor-5 ($S1P_5$) and may have little or at least no substantial agonist activity against other sphingosine-1-phosphate receptors (in a mammal such as a human). The sphingosine-1-phosphate receptor agonist used may, for example, be 5-[3-[(1S)-1-(2-hydroxyethylamino)-2,3-dihydro-1H-inden-4-yl]-1,2,4-oxadiazol-5-yl]-2-propan-2-yloxybenzonitrile (also known as ozanimod and RPC1063) or a pharmaceutically acceptable salt thereof such as but not limited to a hydrochloride salt. The structure of ozanimod is shown below.

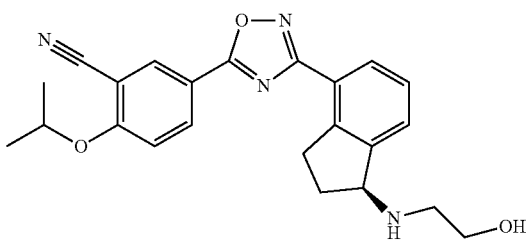 [SMILES: CC(C)Oc1ccc(-c2nc(-c3cccc4c3CC[C@@H]4NCCO)no2)cc1C#N]

See also Scott et al., British Journal of Pharmacology 2016 173:1778-1792.

The sphingosine-1-phosphate receptor agonist may, for example, be etrasimod or a pharmaceutically acceptable salt thereof such as but not limited to a hydrochloride salt. The structure of etrasimod is shown below.

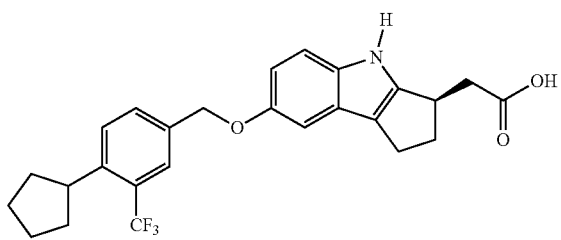 [SMILES: O=C(O)C[C@H]1CCc2c1[nH]c1ccc(OCc3ccc(C4CCCC4)c(C(F)(F)F)c3)cc21]

The sphingosine-1-phosphate receptor agonist may, for example, be amiselimod or a pharmaceutically acceptable salt thereof such as but not limited to a hydrochloride salt. The structure of amiselimod is shown below.

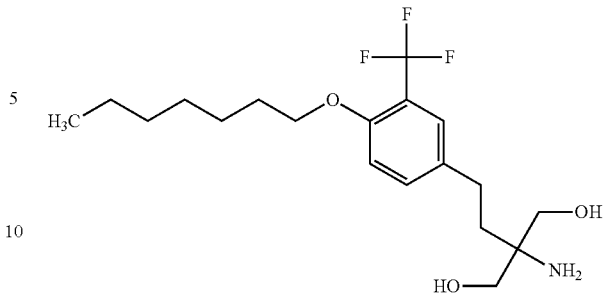

ABC294640 (also known as Yeliva®) used in the experiments presented herein is a reported sphingosine kinase-2 selective inhibitor, namely the compound (7S)-3-(4-chlorophenyl)-N-(pyridin-4-ylmethyl)adamantane-1-carboxamide. The structure of ABC294640 is shown below.

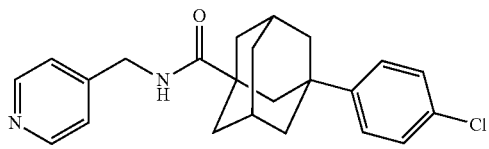 [SMILES: O=C(NCc1ccncc1)C12CC3CC(C1)CC(c1ccc(Cl)cc1)(C3)C2]

See also French et al., J. Pharmacol. Exp. Ther. 2010, 333, 129-139.

Experiments

MTT cell viability assays evaluating the effect of different concentrations of each of ozanimod, ABC294640 and SK1-I on four human hepatocellular carcinoma cell lines, Hep G2, Hep 3B, Huh 7 and PLC-PRF5 were performed. These four cells line were selected for the study because they are among HCC cells lines whose gene expression profiles most closely resemble those of primary HCC tumors. See Chen et al., BMC Medical Genomics 2015, 8(Suppl 2):S5. The following concentrations of the compounds were tested.

Ozanimod: 200 µM, 111.1 µM, 61.73 µM, 34.29 µM, 19.05 µM, 10.58 µM and 0 µM.

ABC294640: 200 µM, 111.1 µM, 61.73 µM, 34.29 µM, 19.05 µM, 10.58 µM and 0 µM.

SK1-I: 20 µM, 11.11 µM, 6.173 µM, 3.429 µM, 1.905 µM, 1.058 µM and 0 µM.

The following MTT assay protocol was followed.

Prepared stock solutions: 50 mM ozanimod, 50 mM ABC294640, 10 mM SK1-I in DMSO.

Plated 20000 cells in 160 µl medium per well in 96-well plates for each cell line and incubated at 37° C. overnight.

Prepared compound serial dilutions: for ozanimod and ABC294640: dilute stock 50 mM 1:50 in medium to 1000 µM; for SK1-I, dilute stock 10 mM 1:50 in medium to 100 µM, them make serial 1:1.8 fold serial dilution to the titration. For negative control, diluted DMSO 1:50 to medium.

Added 40 µl negative control and serially titrated compounds to 160 µl of cells for each cell line. Performed in triplicate for each cell line.

Incubated at 37° C. for 72 hours.

Performed assay using Vybrant MTT Cell Proliferation Assay kit (V-13154) (Molecular Probes) from Thermo Fisher Scientific (Waltham, Mass. USA).

Figure 2:
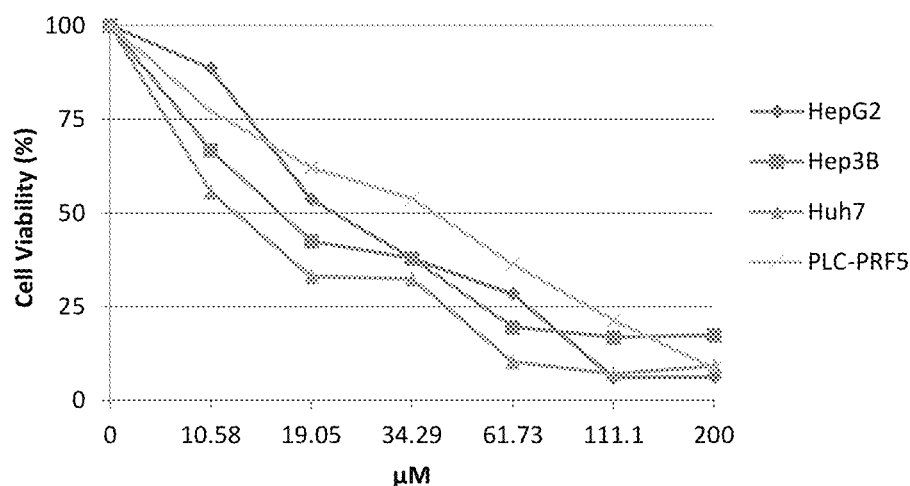
FIG. 2 shows MTT assay data (72 hours) for various concentrations of ABC294640 for four human hepatocellular carcinoma cell lines.
Figure 3:
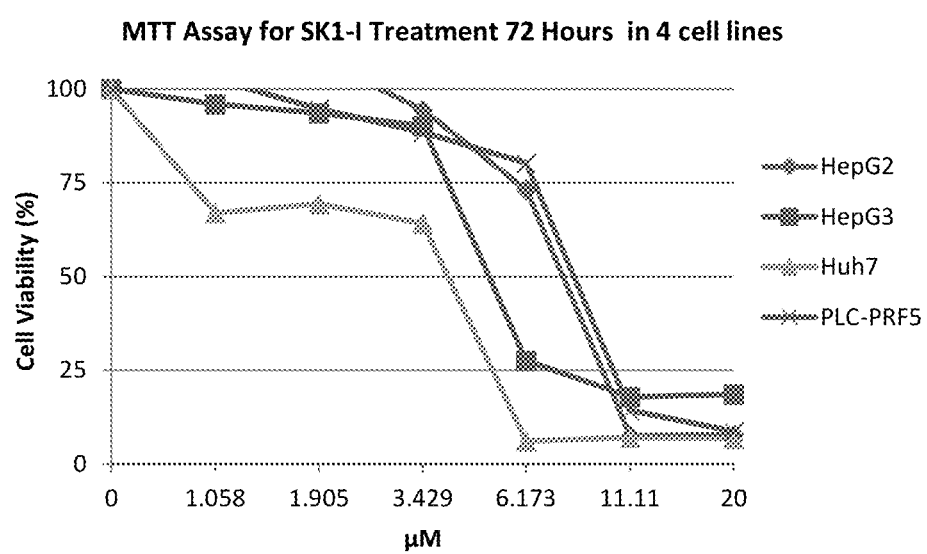
FIG. 3 shows MTT assay data (72 hours) for various concentrations of SK1-I for four human hepatocellular carcinoma cell lines.

The results of these 72-hour treatment MTT assays are shown in FIGS. 1-3 as follows.

FIG. 1 shows the MTT assay data (72 hours) for ozanimod for the four human hepatocellular carcinoma cell lines.

FIG. 2 shows the MTT assay data (72 hours) for ABC294640 for the four human hepatocellular carcinoma cell lines.

FIG. 3 shows the MTT assay data (72 hours) for SK1-I for the four human hepatocellular carcinoma cell lines.

Figure 4A:
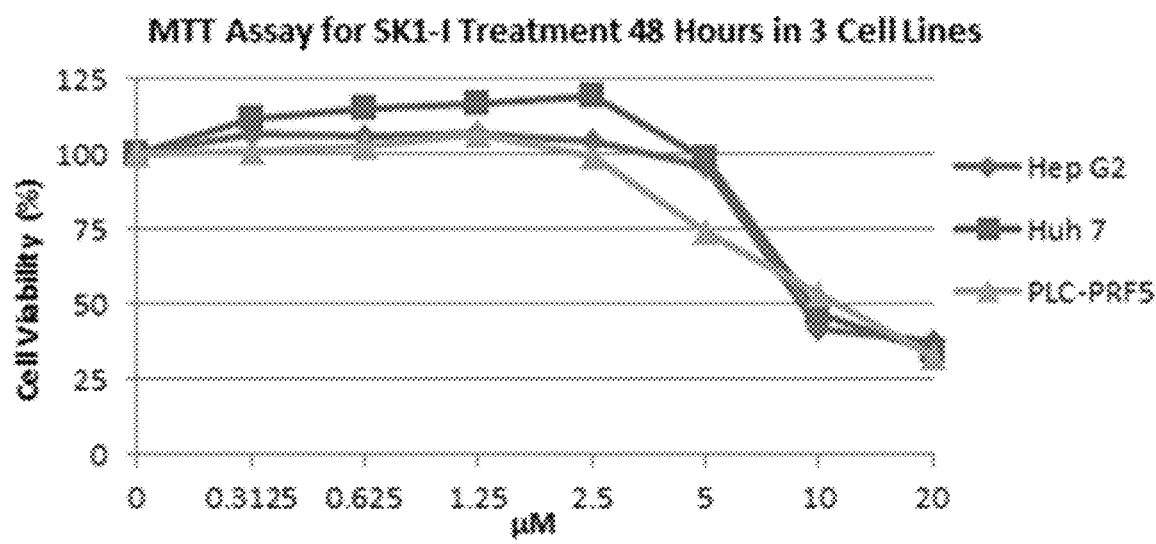
FIG. 4A shows MTT assay data (48 hours) for various concentrations of SK1-I for three human hepatocellular carcinoma cell lines.
Figure 4B:
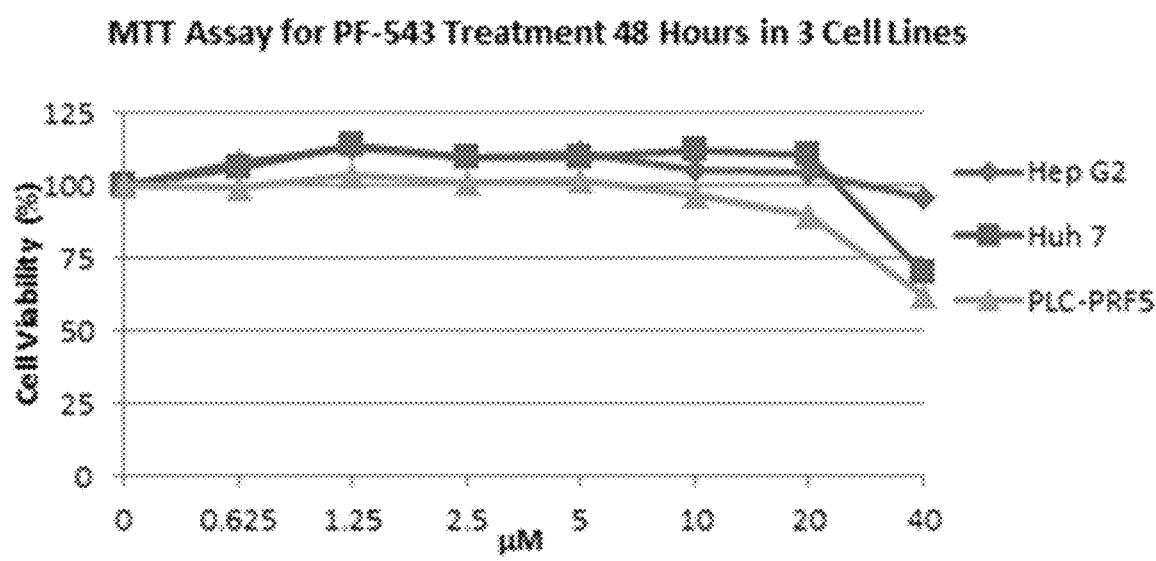
FIG. 4B shows MTT assay data (48 hours) for various concentrations of PF-543, a super potent SphK1 inhibitor, for the same three human hepatocellular carcinoma cell lines shown in FIG. 4A.

48-hour treatment MTT assays were also performed as follows. FIG. 4A shows MTT assay data (48 hours) for various concentrations of SK1-I for three human hepatocellular carcinoma cell lines, Hep G2, Huh 7, and PLC-PRF5. FIG. 4B shows MTT assay data (48 hours) for various concentrations of PF-543, a super potent SphK1 inhibitor (see Schnute et al., Biochem. J. (2012) 444, 79-88), for the same three human hepatocellular carcinoma cell lines shown in FIG. 4A. This data shows that SK1-I is more effective at killing hepatocellular carcinoma cells than PF-543 despite the latter drug's much greater potency in inhibiting SphK1.

Apoptosis/necrosis assays evaluating the effect of different concentrations of each of ozanimod, ABC294640 and SK1-I on the four human hepatocellular carcinoma cell lines, Hep G2, Hep 3B, Huh 7 and PLC-PRF5 were also performed.

The protocol used for the apoptosis assays was:
Plated cells in 6-well plates and incubated at 37° C. overnight.
Prepared concentrations of test compound and control compound DMSO in media.
Ozanimod: 5 μM, 10 μM, and 20 μM.
ABC294640: 10 μM, 20 μM, and 40 μM.
SK1-I: 10 μM, 20 μM, and 40 μM.
Control: 0.2% DMSO.
Aspirated the medium from the 6-well plates and added test compound concentrations in media or 0.2% DMSO control in media. Incubated at 37° C. for 24 hours.
Collected and processed the cells following the flow cytometry protocol of the GFP Certified® Apoptosis/Necrosis detection kit from Enzo Life Sciences, Inc. (product no. ENZ-51002; Farmingdale, N.Y., USA).

FIGS. 5-16 present graphs plotting the data from these 24-hour apoptosis assays for the different concentrations of compounds and no-drug control for the various cell lines. Channel FL2 picks up the apoptosis signal and channel FL3 picks up the necrosis signal. Data points in Quadrant 3 (Q3) in the graphs corresponds to cells undergoing apoptosis (cells positive for the apoptosis detection reagent of the assay). Data points in Quadrant 2 (Q2) in the graphs corresponds to cells that are positive for the apoptosis detection reagent and positive for the necrosis detection reagent of the assay (indicative of late-stage apoptosis).

Figure 5B:
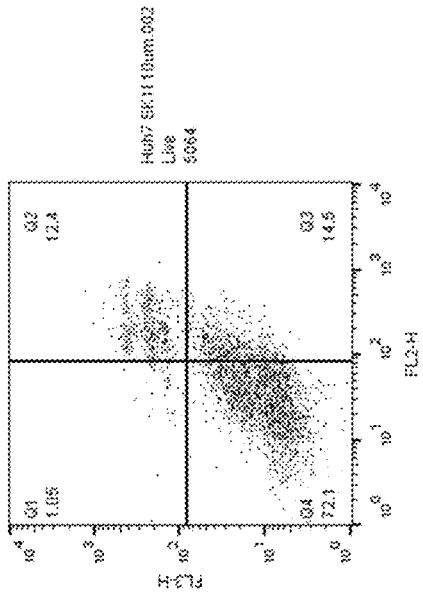
FIGS. 5A-D show apoptosis assay data for various concentrations of SK1-I and no-drug control for Huh7 cells. SK1-I strongly induced apoptosis in the Huh7 cells.
Figure 5D:
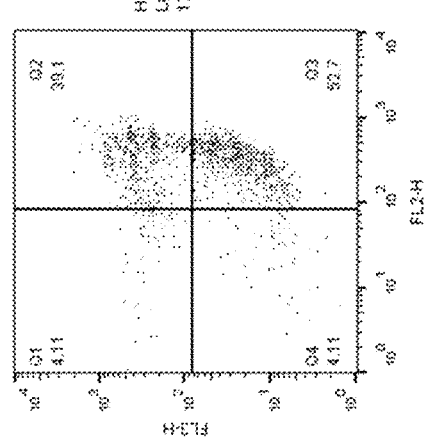
Figure 5A:
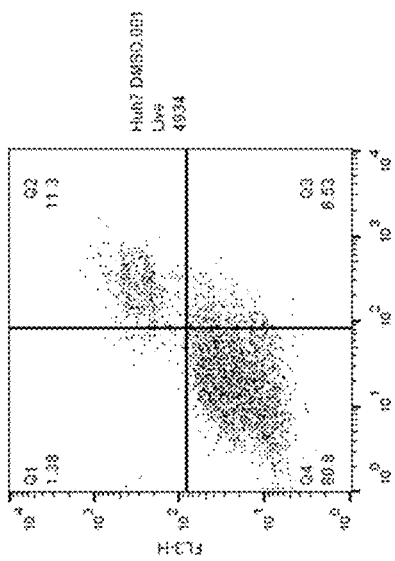
Figure 5C:
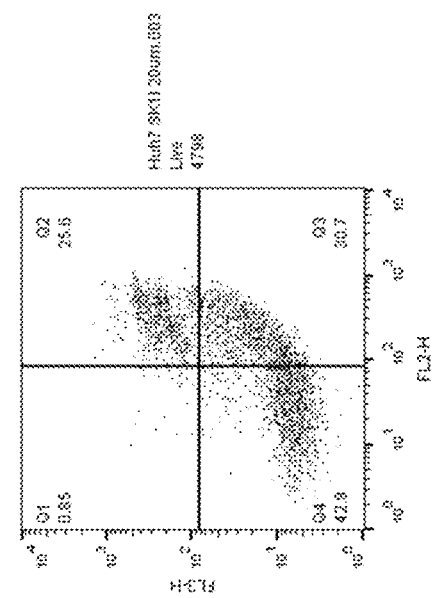

FIGS. 5A-D show the apoptosis assay data for various concentrations of SK1-I and no-drug control for Huh7 cells. FIG. 5A shows the results for no-drug control. FIG. 5B shows the results for treatment with 10 μM SK1-I. FIG. 5C shows the results for treatment with 20 μM SK1-I. FIG. 5D shows the results for treatment with 40 μM SK1-I. SK1-I strongly induced apoptosis in the Huh7 cells.

FIGS. 6A-D show the apoptosis assay data for various concentrations of SK1-I and no-drug control for PLC-PRF5 cells. FIG. 6A shows the results for no-drug control. FIG. 6B shows the results for treatment with 10 μM SK1-I. FIG. 6C shows the results for treatment with 20 μM SK1-I. FIG. 6D shows the results for treatment with 40 μM SK1-I. SK1-I strongly induced apoptosis in the PLC-PRF5 cells.

FIGS. 7A-D show the apoptosis assay data for various concentrations of SK1-I and no-drug control for Hep 3B cells. FIG. 7A shows the results for no-drug control. FIG. 7B shows the results for treatment with 10 μM SK1-I. FIG. 7C shows the results for treatment with 20 μM SK1-I. FIG. 7D shows the results for treatment with 40 μM SK1-I. SK1-I strongly induced apoptosis in the Hep 3B cells.

FIGS. 8A-D show the apoptosis assay data for various concentrations of SK1-I and no-drug control for Hep G2 cells. FIG. 8A shows the results for no-drug control. FIG. 8B shows the results for treatment with 10 μM SK1-I. FIG. 8C shows the results for treatment with 20 μM SK1-I. FIG. 8D shows the results for treatment with 40 μM SK1-I. SK1-I strongly induced apoptosis in the Hep G2 cells.

Figure 9B:
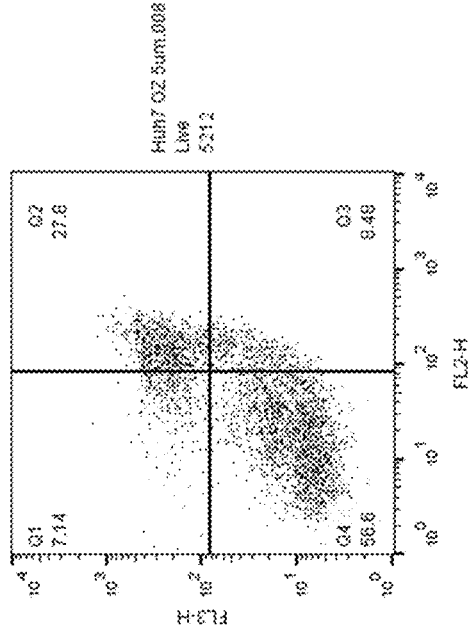
FIGS. 9A-D show apoptosis assay data for various concentrations of ozanimod and no-drug control for Huh7 cells. Ozanimod strongly induced apoptosis in the Huh7 cells.
Figure 9D:
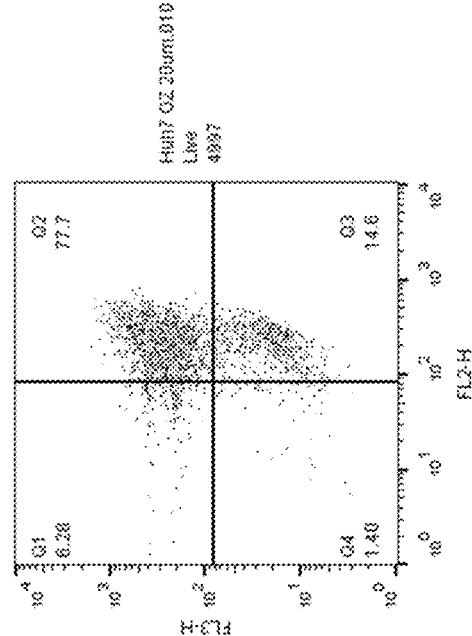
Figure 9A:
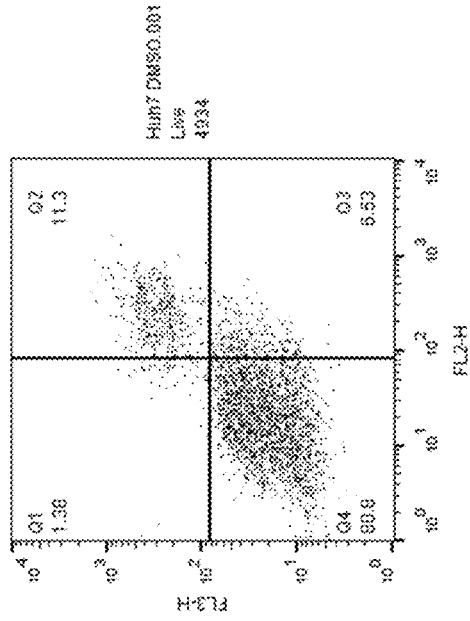
Figure 9C:
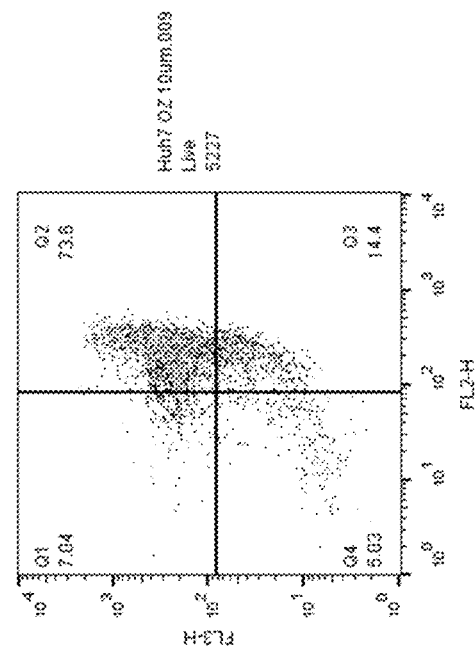

FIGS. 9A-D show the apoptosis assay data for various concentrations of ozanimod and no-drug control for Huh7 cells. FIG. 9A shows the results for no-drug control. FIG. 9B shows the results for treatment with 5 μM ozanimod. FIG. 9C shows the results for treatment with 10 μM ozanimod. FIG. 9D shows the results for treatment with 20 μM ozanimod. Ozanimod strongly induced apoptosis in the Huh7 cells.

Figure 10B:
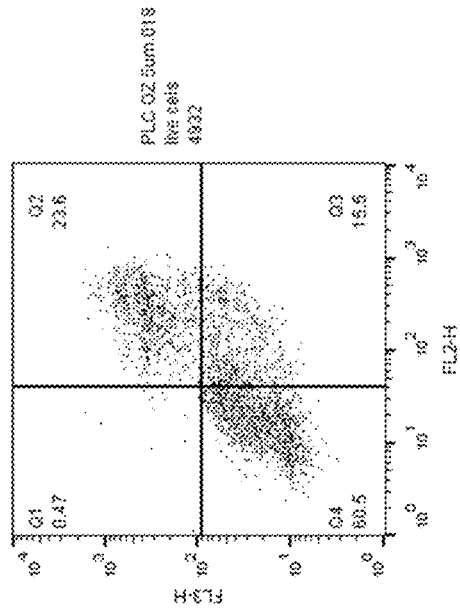
FIGS. 10A-D show apoptosis assay data for various concentrations of ozanimod and no-drug control for PLC-PRF5 cells. Ozanimod strongly induced apoptosis in the PLC-PRF5 cells.
Figure 10D:
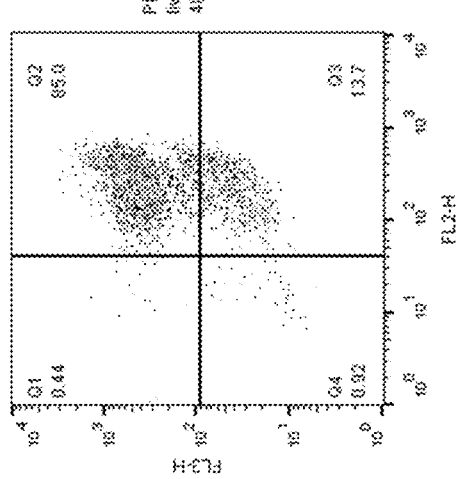
Figure 10A:
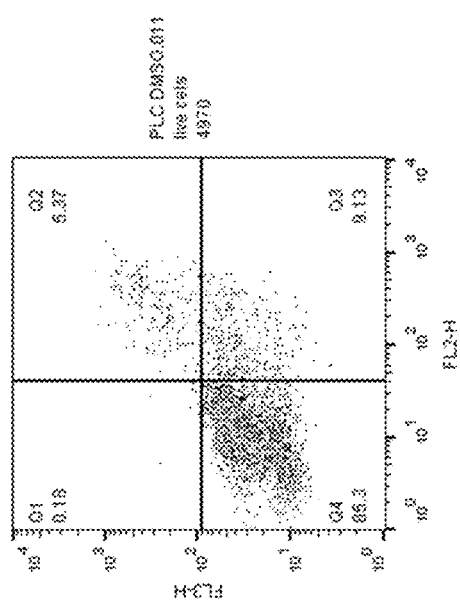
Figure 10C:
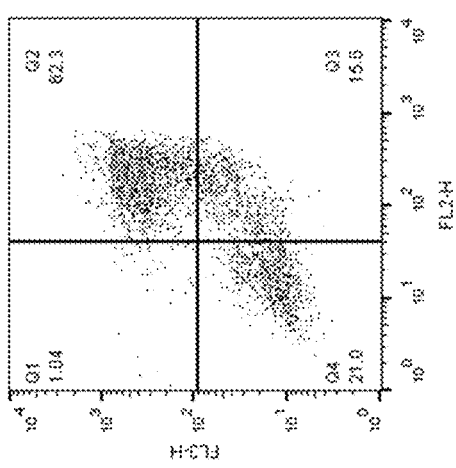

FIGS. 10A-D show the apoptosis assay data for various concentrations of ozanimod and no-drug control for PLC-PRF5 cells. FIG. 10A shows the results for no-drug control. FIG. 10B shows the results for treatment with 5 μM ozanimod. FIG. 10C shows the results for treatment with 10 μM ozanimod. FIG. 10D shows the results for treatment with 20 μM ozanimod. Ozanimod strongly induced apoptosis in the PLC-PRF5 cells.

FIGS. 11A-D show the apoptosis assay data for various concentrations of ozanimod and no-drug control for Hep 3B cells. FIG. 11A shows the results for no-drug control. FIG. 11B shows the results for treatment with 10 μM ozanimod. FIG. 11C shows the results for treatment with 20 μM ozanimod. FIG. 11D shows the results for treatment with 40 μM ozanimod. Ozanimod strongly induced apoptosis in the Hep 3B cells.

FIGS. 12A-D show the apoptosis assay data for various concentrations of ozanimod and no-drug control for Hep G2 cells. FIG. 12A shows the results for no-drug control. FIG. 12B shows the results for treatment with 10 μM ozanimod. FIG. 12C shows the results for treatment with 20 μM ozanimod. FIG. 12D shows the results for treatment with 40 μM ozanimod. Ozanimod strongly induced apoptosis in the Hep G2 cells.

FIGS. 13A-D show the apoptosis assay data for various concentrations of ABC294640 and no-drug control for Huh7 cells. FIG. 13A shows the results for no-drug control. FIG. 13B shows the results for treatment with 10 μM ABC294640. FIG. 13C shows the results for treatment with 20 μM ABC294640. FIG. 13D shows the results for treatment with 40 μM ABC294640. ABC294640 failed to induce apoptosis in the Huh7 cells.

FIGS. 14A-D show the apoptosis assay data for various concentrations of ABC294640 and no-drug control for PLC-PRF5 cells. FIG. 14A shows the results for no-drug control. FIG. 14B shows the results for treatment with 10 μM ABC294640. FIG. 14C shows the results for treatment with 20 μM ABC294640. FIG. 14D shows the results for treatment with 40 μM ABC294640. ABC294640 did not substantially induce apoptosis in the PLC-PRF5 cells.

FIGS. 15A-D show the apoptosis assay data for various concentrations of ABC294640 and no-drug control for Hep 3B cells. FIG. 15A shows the results for no-drug control. FIG. 15B shows the results for treatment with 10 μM ABC294640. FIG. 15C shows the results for treatment with 20 μM ABC294640. FIG. 15D shows the results for treatment with 40 μM ABC294640. ABC294640 did not substantially induce apoptosis in the Hep 3B cells.

FIGS. 16A-D show the apoptosis assay data for various concentrations of ABC294640 and no-drug control for Hep G2 cells. FIG. 16A shows the results for no-drug control. FIG. 16B shows the results for treatment with 10 μM ABC294640. FIG. 16C shows the results for treatment with 20 μM ABC294640. FIG. 16D shows the results for treatment with 40 μM ABC294640. ABC294640 failed to induce apoptosis in the Hep G2 cells.

Figures 17A, 17B, 17C:
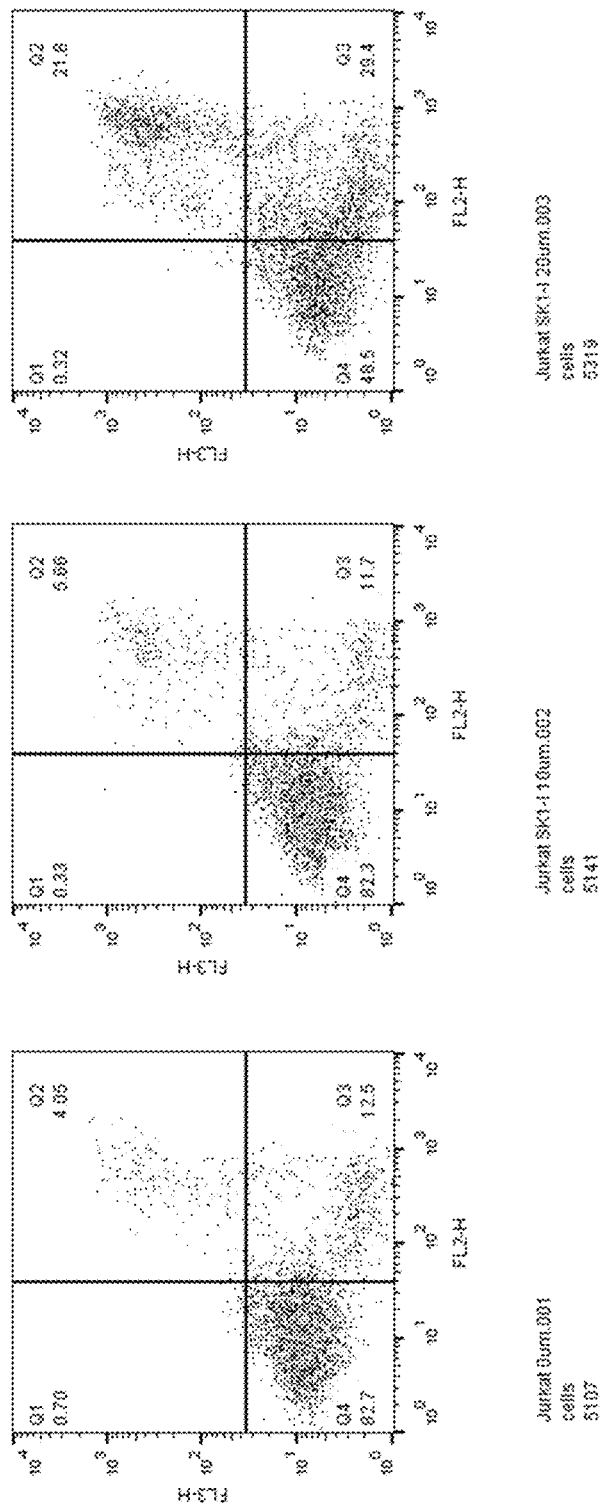
FIGS. 17A-C show apoptosis assay data for various concentrations of SK1-I and no-drug control for Jurkat cells (human T-cell leukemia cell line). SK1-I strongly induced apoptosis in the Jurkat cells.

FIGS. 17A-C show apoptosis assay data for various concentrations of SK1-I and no-drug control for Jurkat cells (human T-cell leukemia cell line). FIG. 17A shows the results for no-drug control. FIG. 17B shows the results for treatment with 10 μM SK1-I. FIG. 17C shows the results for treatment with 20 μM SK1-I. SK1-I strongly induced apoptosis in the Jurkat cells.

Figures 18A, 18B, 18C:
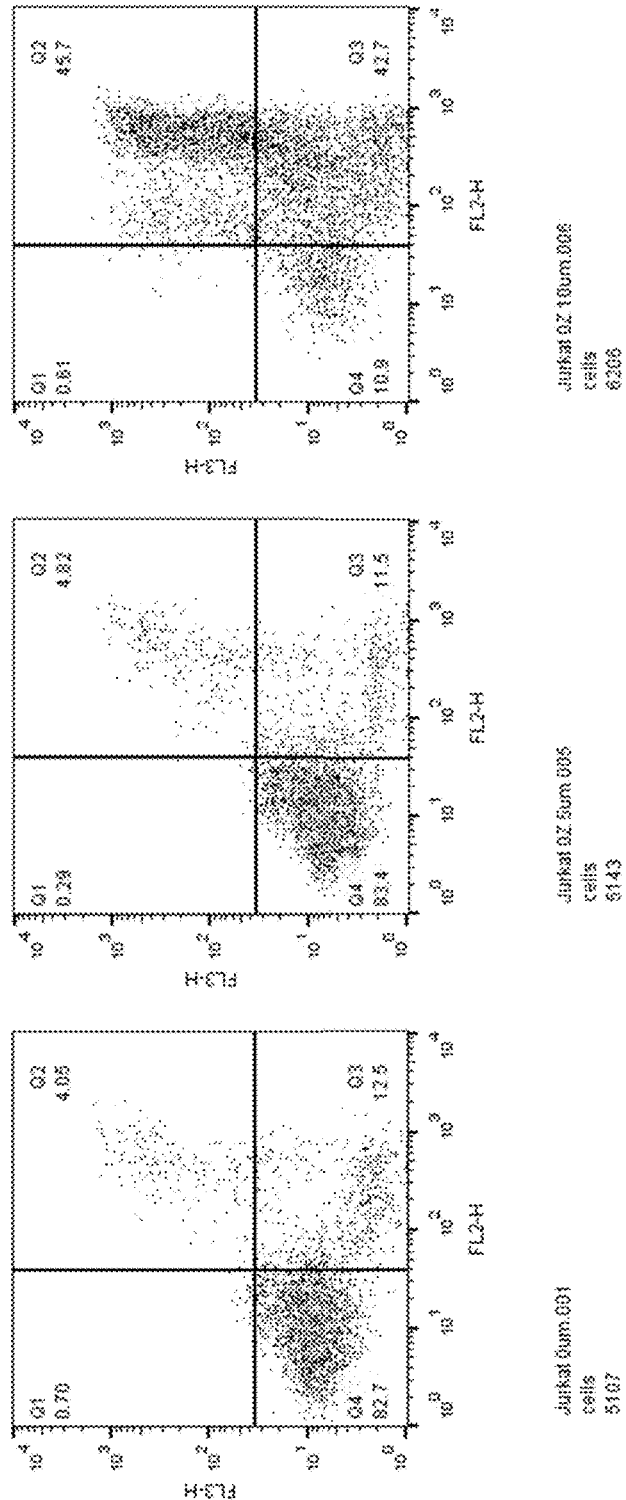
FIGS. 18A-C show apoptosis assay data for various concentrations of ozanimod and no-drug control for Jurkat cells. Ozanimod strongly induced apoptosis in the Jurkat cells.

FIGS. 18A-C show apoptosis assay data for various concentrations of ozanimod and no-drug control for Jurkat cells. FIG. 18A shows the results for no-drug control. FIG. 18B shows the results for treatment with 5 μM ozanimod. FIG. 18C shows the results for treatment with 10 μM ozanimod. Ozanimod strongly induced apoptosis in the Jurkat cells.

In still further experiments, the effects of SK1-I and ozanimod on normal (non-cancerous) primary human hepatocytes were investigated. Fresh human hepatocytes in a 12-well plate (HUF12) were obtained from Triangle Research Labs (Durham, N.C., USA; part of Lonza Group) and handled according to the supplier's protocol. The shipping medium was aspirated from each well and replaced with 1 ml per well of warm Hepatocyte Maintenance Medium. The plate was then placed in a 5% $CO_2$ incubator at 37° C. and the hepatocytes were allowed to acclimate overnight. The Hepatocyte Maintenance Medium was replaced before treatment with drug or no-drug control, and the hepatocytes were treated with 0 μM (no-drug control), 10 μM, 20 μM, or 40 μM SK1-I or 0 μM, 2.5 μM, 5 μM, or 10 μM ozanimod for 24 hours under incubation. The cells were then harvested and analyzed using the GFP Certified® Apoptosis/Necrosis detection kit. The results are shown in FIGS. 19A-D for SK1-I and FIGS. 20A-D for ozanimod as follows.

Figures 19A, 19B:
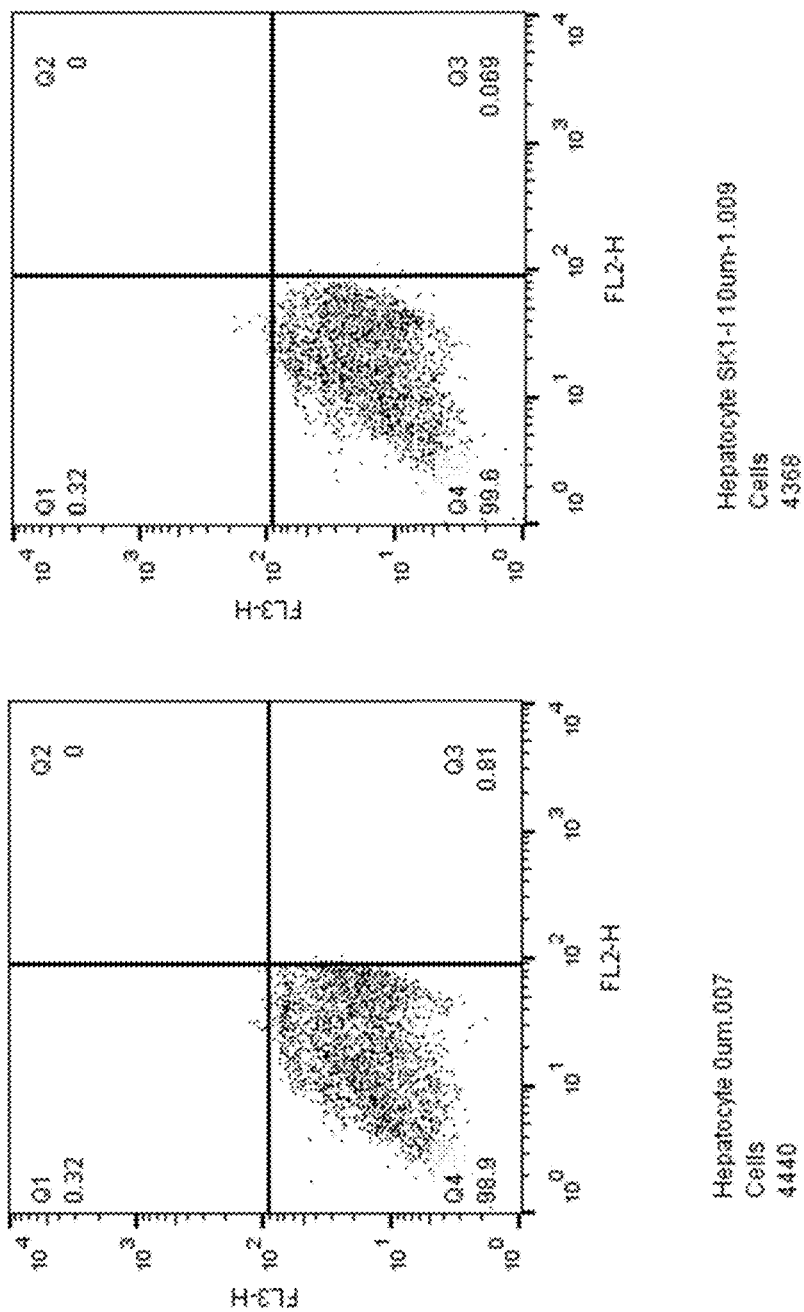
FIGS. 19A-D show apoptosis assay data for various concentrations of SK1-I and no-drug control for primary human hepatocytes. SK1-I did not induce apoptosis of the primary human hepatocytes at any concentration tested.
Figure 19D:
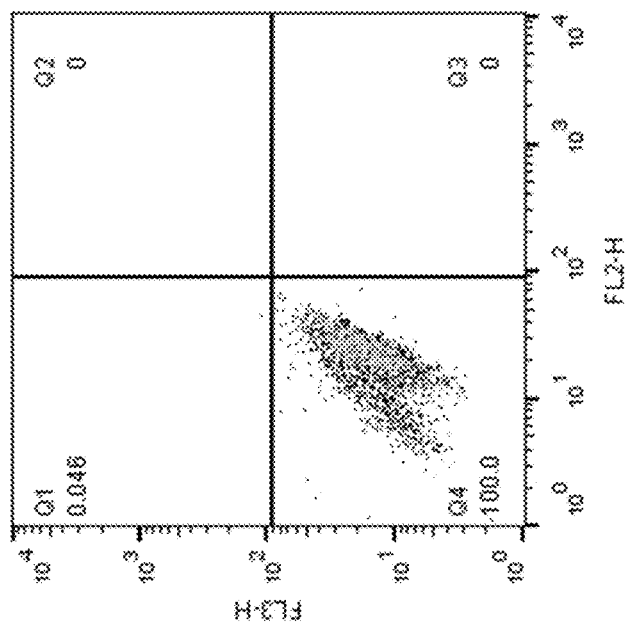
Figure 19C:
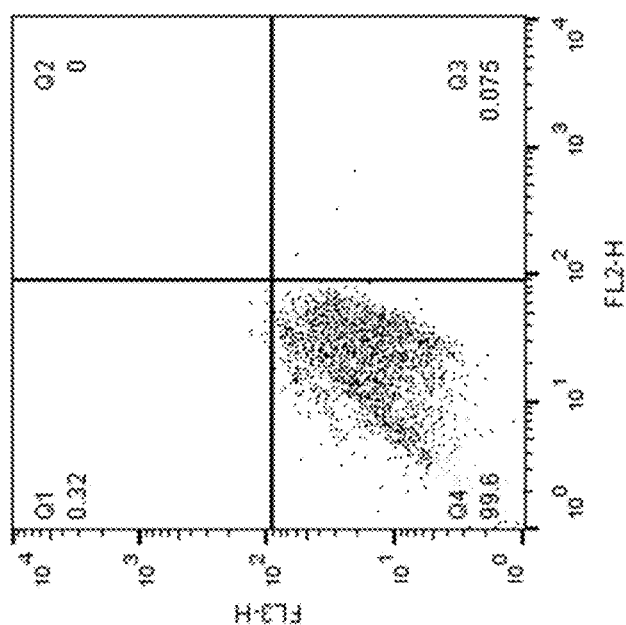

FIGS. 19A-D show apoptosis assay data for various concentrations of SK1-I and no-drug control for primary human hepatocytes. FIG. 19A shows the results for no-drug control. FIG. 19B shows the results for treatment with 10 μM SK1-I. FIG. 19C shows the results for treatment with 20 μM SK1-I. FIG. 19D shows the results for treatment with 40 μM SK1-I. SK1-I did not induce apoptosis of the primary human hepatocytes at any concentration tested.

Figures 20A, 20B:
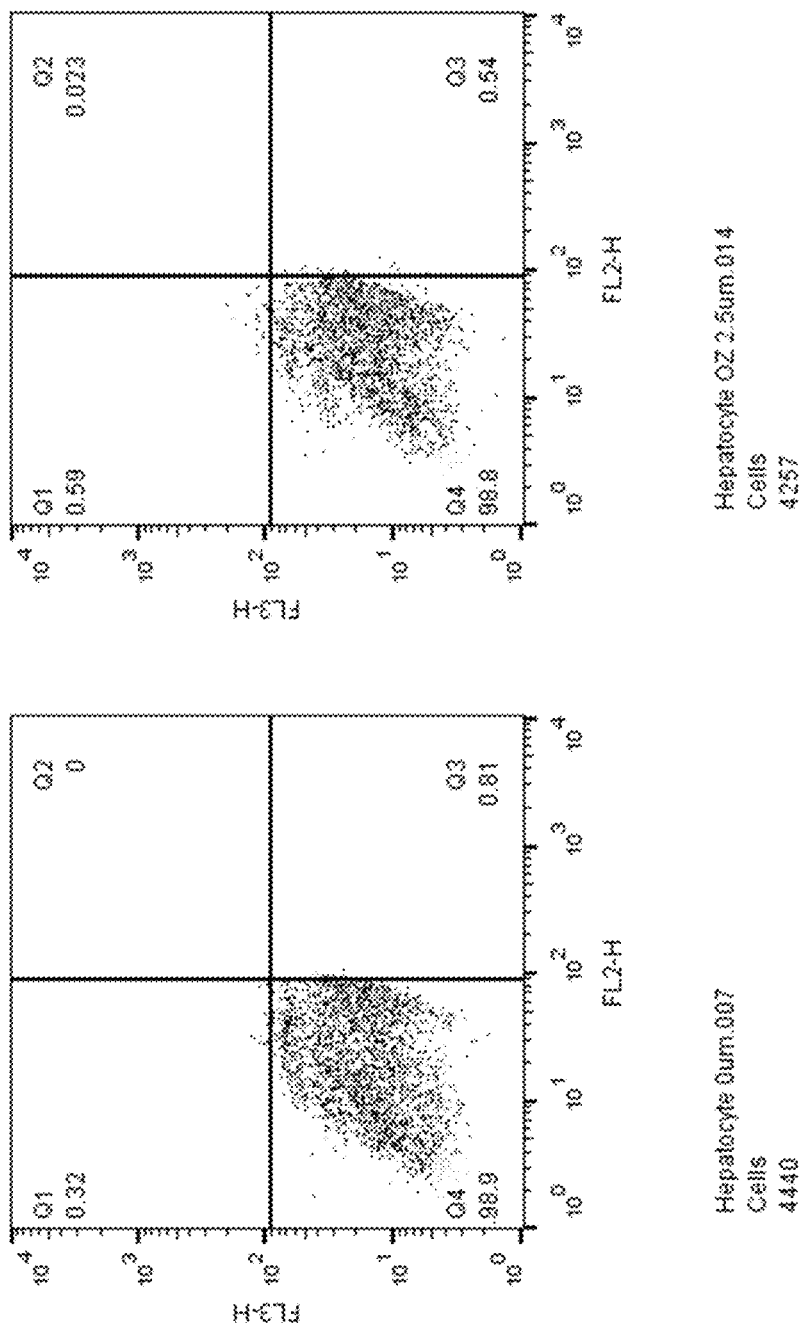
FIGS. 20A-D show apoptosis assay data for various concentrations of ozanimod and no-drug control for primary human hepatocytes. Ozanimod did not induce apoptosis of the primary human hepatocytes at any concentration tested.
Figures 20C, 20D:
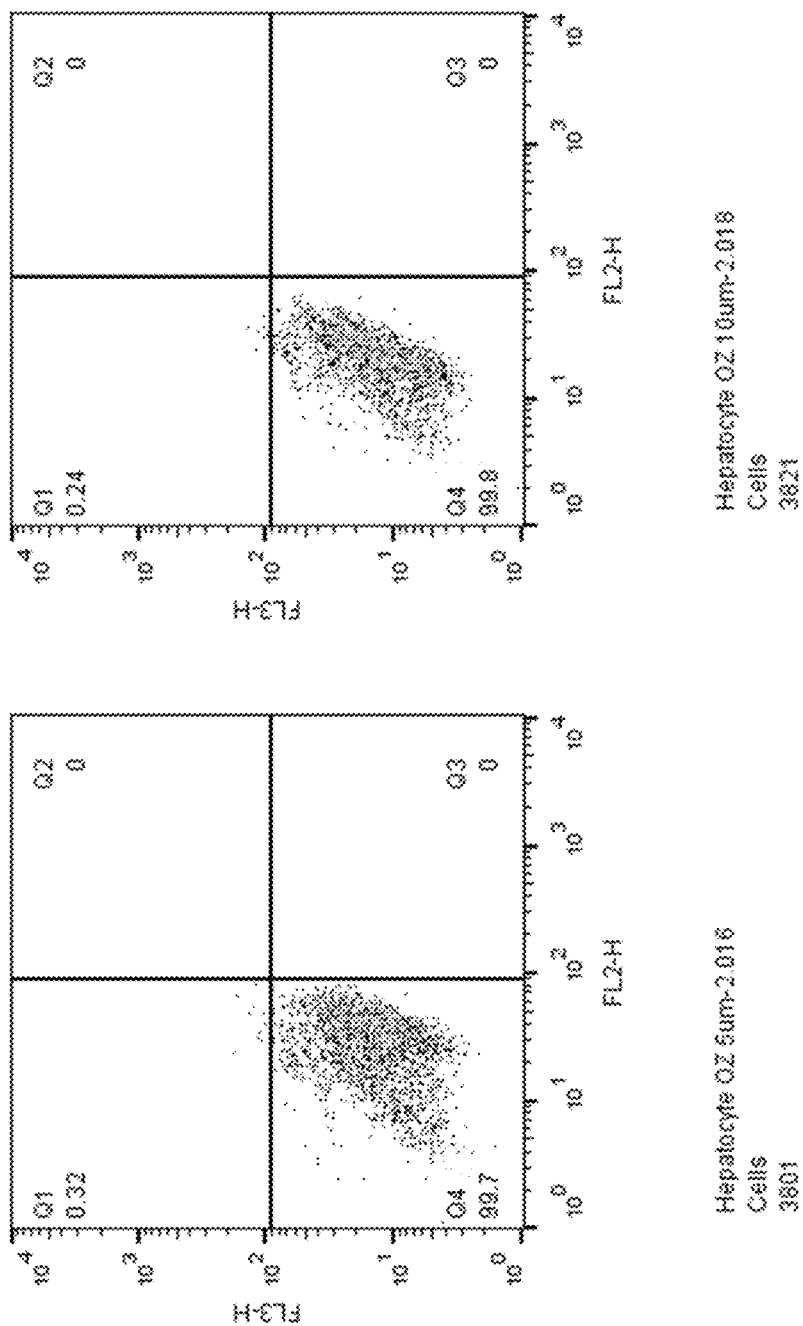

FIGS. 20A-D show apoptosis assay data for various concentrations of ozanimod and no-drug control for primary human hepatocytes. FIG. 20A shows the results for no-drug control. FIG. 20B shows the results for treatment with 2.5 μM ozanimod. FIG. 20C shows the results for treatment with 5 μM ozanimod. FIG. 20D shows the results for treatment with 10 μM ozanimod. Ozanimod did not induce apoptosis of the primary human hepatocytes at any concentration tested.

Without limitation, the following embodiments are also provided.

Embodiments Involving Sphingosine Kinase 1 (SphK1) Inhibitors

Embodiment 1. A method for treating liver cancer in a mammalian subject, such as a human, including the step of:
administering to a mammalian subject in need of treatment for liver cancer, an effective amount of a sphingosine kinase type I inhibitor.

Embodiment 2. The method of embodiment 1, wherein the liver cancer is hepatic cell carcinoma (HCC).

Embodiment 3. The pharmaceutical composition of embodiment 1, wherein the liver cancer is selected from the group consisting of fibrolamellar HCC, cholangiocarcinoma (bile duct cancer) and angiosarcoma.

Embodiment 4. The method of any one of the preceding embodiments, wherein the sphingosine kinase type I inhibitor at least substantially does not inhibit sphingosine kinase type II.

Embodiment 5. The method of any one of the preceding embodiments, wherein the sphingosine kinase type I inhibitor includes a sphingosine kinase type I inhibitor disclosed in U.S. Pat. Nos. 8,372,888 and/or 8,314,151, or a pharmaceutically acceptable salt thereof.

Embodiment 6. The method of any one of embodiments 1-5, wherein the sphingosine kinase type I inhibitor includes SK1-I or a pharmaceutically acceptable salt thereof.

Embodiment 7. The method of any one of the preceding embodiments, wherein said administration includes parenteral administration.

Embodiment 8. The method of embodiment 7, wherein said administration is via injection, such as intravenous injection, intramuscular injection, or subcutaneous injection.

Embodiment 9. The method of any one of embodiments 1-6, wherein said administration includes non-parenteral administration.

Embodiment 10. The method of any one of embodiments 1-6, wherein said administration includes oral administration by ingestion.

Embodiment 11. The method of embodiment 10, wherein said oral administration includes administering a dosage form including the sphingosine kinase type I inhibitor and at least one pharmaceutically acceptable excipient.

Embodiment 12. The method of embodiment 11, wherein the dosage form is selected from the group consisting of a tablet, a capsule, and a gel cap.

Embodiment 13. The method of any one of embodiments 1-6, wherein said administration includes administration via the alimentary canal.

Embodiment 14. The method of any one of the preceding embodiments, further including the step of:
co-administering to the subject an effective amount of ozanimod or a pharmaceutically acceptable salt thereof.

Embodiment 15. A pharmaceutical composition for the treatment of a liver cancer in a mammalian subject, such as a human, including:
a therapeutically effective amount of a sphingosine kinase type I inhibitor.

Embodiment 16. The pharmaceutical composition of embodiment 15, wherein the liver cancer is hepatic cell carcinoma (HCC).

Embodiment 17. The pharmaceutical composition of embodiment 15, wherein the liver cancer is selected from the group consisting of Fibrolamellar HCC, Cholangiocarcinoma (bile duct cancer) and Angiosarcoma.

Embodiment 18. The pharmaceutical composition of any one of the preceding embodiments, wherein the sphingosine kinase type I inhibitor at least substantially does not inhibit sphingosine kinase type II.

Embodiment 19. The pharmaceutical composition of any one of the preceding embodiments, wherein the sphingosine kinase type I inhibitor includes a sphingosine kinase type I inhibitor disclosed in U.S. Pat. Nos. 8,372,888 and/or 8,314, 151, or a pharmaceutically acceptable salt thereof.

Embodiment 20. The pharmaceutical composition of any one of embodiment 15-18, wherein the sphingosine kinase type I inhibitor includes SK1-I or a pharmaceutically acceptable salt thereof.

Embodiment 21. The pharmaceutical composition of any one of the preceding embodiments, wherein said composition is for parenteral administration.

Embodiment 22. The pharmaceutical composition of embodiment 21, wherein said composition is for administration via injection, such as intravenous injection, intramuscular injection, or subcutaneous injection.

Embodiment 23. The pharmaceutical composition of any one of embodiments 15-20, wherein said composition is for non-parenteral administration.

Embodiment 24. The pharmaceutical composition of any one of embodiments 15-20, wherein said composition is for oral administration by ingestion.

Embodiment 25. The pharmaceutical composition of any one of embodiment 15-24, further including at least one pharmaceutically acceptable excipient.

Embodiment 26. The pharmaceutical composition of any one of embodiments 15-25, wherein said composition is a solid dosage form.

Embodiment 27. The pharmaceutical composition of embodiment 24, provided in a dosage form selected from the group consisting of a liquid, a tablet, a capsule, and a gel cap.

Embodiment 28. The pharmaceutical composition of any one of embodiments 15-20, wherein said composition is for administration via the alimentary canal.

Embodiment 29. The pharmaceutical composition of any one of embodiments 15-28, further including a therapeutically effective amount of ozanimod or a pharmaceutically acceptable salt thereof.

Embodiment 30. A method for inducing apoptosis of mammalian liver cancer cells, such as hepatocellular carcinoma (HCC) cells, including the step of:

contacting the mammalian liver cancer cells with an effective amount of a selective sphingosine kinase type I inhibitor, such as any of those disclosed in U.S. Pat. Nos. 8,372,888 and/or 8,314,151, such as SK1-I, or a pharmaceutically acceptable salt thereof.

Embodiment 31. Use of a selective sphingosine kinase type I inhibitor, such as any of those disclosed in U.S. Pat. Nos. 8,372,888 and/or 8,314,151, such as SK1-I, or a pharmaceutically acceptable salt thereof, for inducing apoptosis of mammalian liver cancer cells, such as hepatocellular carcinoma (HCC) cells.

Embodiments Involving Sphingosine-1-Phosphate Receptor Agonists

Embodiment 32. A method for treating a cancer or a myleoproilferative disorder (myeloproliferative neoplasm) in a mammalian subject, such as a human, including the step of:

administering to a mammalian subject in need of treatment for a cancer or myeloproliferative disorder, a therapeutically effective amount of a sphingosine-1-phosphate receptor agonist, such as an agonist of one or both of sphingosine-1-phosphate receptor-1 ($S1P_1$) and sphingosine-1-phosphate receptor-5 ($S1P_5$) such as ozanimod (RPC1063) or a pharmaceutically acceptable salt thereof.

Embodiment 33. The method of embodiment 32, wherein the myeloproliferative disorders is selected from the group consisting of: Chronic myelogenous leukemia (e.g, BCR-ABL1-positive); Chronic neutrophilic leukemia; Polycythemia vera; Primary myelofibrosis; Essential thrombocythemia; Chronic eosinophilic leukemia (not otherwise specified); and Mastocytosis.

Embodiment 34. The method of embodiment 32, wherein said cancer is a hematological malignancy.

Embodiment 35. The method of embodiment 34, wherein said hematological malignancy is selected from the group consisting of: leukemias, lymphomas and myelomas.

Embodiment 36. The method of embodiment 35, wherein said hematological malignancy is selected from the group consisting of: Acute lymphoblastic leukemia (ALL); Acute myelogenous leukemia (AML); Chronic lymphocytic leukemia (CLL); Chronic myelogenous leukemia (CML); Acute monocytic leukemia (AMoL); Hodgkin's lymphomas (e.g., any of main four subtypes); and Non-Hodgkin's lymphomas (any subtype).

Embodiment 37. The method of embodiment of embodiment 32, wherein said cancer is a solid organ cancer.

Embodiment 38. The method of embodiment 32, wherein the solid organ cancer is selected from the group consisting of: Adipose tissue cancers such as Liposarcoma, Myxoid liposarcoma adipose; Bladder cancer; Bone cancers such as Chondroblastoma, Chordoma, Ewings sarcoma, Osteosarcoma, Spindle cell tumor; Brain tumors such as Ganglioneuroblastoma, Ganglioneuroma, Glioblastoma, Malignant peripheral nerve sheath tumor, Neuroblastoma, Neurofibroma, Schwannoma brain; Connective tissue cancers such as Chondromyxoid fibroma, Chondrosarcoma, Dedifferentiated chondrosarcoma, Fibromatosis, Monophasic synovial sarcoma; Esophageal adenocarcinoma; Oral squamous cell carcinoma; Kidney cancers such as Kidney carcinoma, Renal cell carcinoma; Liver cancers such as Hepatocellular carcinoma (HCC), Fibrolamellar HCC, Cholangiocarcinoma (bile duct cancer) and Angiosarcoma; Lung cancer such as NSCLC, SCLC; Uterine tumors; Head and Neck cancers such as head and neck squamous cell carcinoma; Ovarian tumors; Prostate cancer; Muscle tissue cancers such as Acute quadriplegic myopathy; Skin cancers such as Melanoma, Sarcoma, Kaposi sarcoma; Alveolar rhabdomyo sarcoma, Embryonal rhabdomyo sarcoma, Leiomyosarcoma; Germ cell tumors such as of the testes, testicular cancer; and Thyroid cancer such as Thyroid adenocarcinoma.

Embodiment 39. The method of embodiment 33, wherein the solid organ cancer is liver cancer.

Embodiment 40. The method of embodiment 39, wherein the liver cancer is hepatic cell carcinoma (HCC).

Embodiment 41. The method of any one of embodiments 32-40, wherein the sphingosine-1-phosphate receptor agonist at least substantially does not agonize sphingosine-1-phosphate receptors other than types-1 and -5.

Embodiment 42. The method of any one of embodiments 32-41, wherein the sphingosine-1-phosphate receptor agonist includes a sphingosine-1-phosphate receptor agonist disclosed in any of U.S. Pub. Nos. 20110172202, 20130231326, and 20150299149 or a pharmaceutically acceptable salt thereof.

Embodiment 43. The method of any one of embodiments 32-42, wherein the sphingosine-1-phosphate receptor agonist includes ozanimod or a pharmaceutically acceptable salt thereof.

Embodiment 44. The method of any one of embodiments 32-43, wherein said administration includes parenteral administration.

Embodiment 45. The method of embodiment 44, wherein said administration is via injection, such as intravenous injection, intramuscular injection, or subcutaneous injection.

Embodiment 46. The method of any one of embodiments 32-43, wherein said administration includes non-parenteral administration.

Embodiment 47. The method of any one of embodiments 32-43, wherein said administration includes oral administration by ingestion.

Embodiment 48. The method of embodiment 47, wherein said oral administration includes administering a dosage form including the sphingosine-1-phosphate receptor agonist and at least one pharmaceutically acceptable excipient.

Embodiment 49. The method of embodiment 48, wherein the dosage form is selected from the group consisting of a liquid, a tablet, a capsule, and a gel cap.

Embodiment 50. The method of any one of embodiments 32-43, wherein said administration includes administration via the alimentary canal.

Embodiment 51. The method of any one of embodiments 32-50, further including the step of:
co-administering to the subject an effective amount of a sphingosine kinase type I inhibitor, such as SK1-I, or a pharmaceutically acceptable salt thereof.

Embodiment 52. The method of any one of embodiments 32-51, further including the step of:
co-administering to the subject a therapeutically effective amount of a cellular ceramide generation promoter, such as 6-[(2S,4R,6E)-4-Methyl-2-(methylamino)-3-oxo-6-octenoic acid]cyclosporin D (Valspodor; PSC833) or a pharmaceutically acceptable salt thereof.

Embodiment 53. The method of any one of embodiments 32-52, further including the step of:
coadministering to the subject a therapeutically effective amount of ceramide.

Embodiment 54. A pharmaceutical composition for the treatment of a cancer or a myeloproliferative disorder (myeloproliferative neoplasm) in a mammalian subject, such as a human, including:
a therapeutically effective amount of a sphingosine-1-phosphate receptor agonist, such as an agonist of one or both of sphingosine-1-phosphate receptor-1 ($S1P_1$) and sphingosine-1-phosphate receptor-5 ($S1P_5$) such as ozanimod (RPC1063) or a pharmaceutically acceptable salt thereof.

Embodiment 55. The pharmaceutical composition of embodiment 54, wherein the myeloproliferative disorders is selected from the group consisting of: Chronic myelogenous leukemia (BCR-ABL1-positive); Chronic neutrophilic leukemia; Polycythemia vera; Primary myelofibrosis; Essential thrombocythemia; Chronic eosinophilic leukemia (not otherwise specified); and Mastocytosis.

Embodiment 56. The pharmaceutical composition of embodiment 54, wherein said cancer is a hematological malignancy.

Embodiment 57. The pharmaceutical composition of embodiment 56, wherein said hematological malignancy is selected from the group consisting of: leukemias, lymphomas and myelomas.

Embodiment 58. The pharmaceutical composition of embodiment 57, wherein said hematological malignancy is selected from the group consisting of: Acute lymphoblastic leukemia (ALL); Acute myelogenous leukemia (AML); Chronic lymphocytic leukemia (CLL); Chronic myelogenous leukemia (CML); Acute monocytic leukemia (AMoL); Hodgkin's lymphomas (e.g., any of main four subtypes); and Non-Hodgkin's lymphomas (any subtype).

Embodiment 59. The pharmaceutical composition of embodiment of embodiment 54, wherein said cancer is a solid organ cancer.

Embodiment 60. The pharmaceutical composition of embodiment 59, wherein the solid organ cancer is selected from the group consisting of: Adipose tissue cancers such as Liposarcoma, Myxoid liposarcoma adipose; Bladder cancer; Bone cancers such as Chondroblastoma, Chordoma, Ewings sarcoma, Osteosarcoma, Spindle cell tumor; Brain tumors such as Ganglioneuroblastoma, Ganglioneuroma, Malignant peripheral nerve sheath tumor, Neuroblastoma, Neurofibroma, Schwannoma brain; Connective tissue cancers such as Chondromyxoid fibroma, Chondrosarcoma, Dedifferentiated chondrosarcoma, Fibromatosis, Monophasic synovial sarcoma; Esophageal adenocarcinoma; Oral squamous cell carcinoma; Kidney cancers such as Kidney carcinoma, Renal cell carcinoma; Liver cancers such as Hepatocellular carcinoma (HCC), Fibrolamellar HCC, Cholangiocarcinoma (bile duct cancer) and Angiosarcoma; Lung cancer such as NSCLC, SCLC; Uterine tumors; Head and Neck cancers such as head and neck squamous cell carcinoma; Ovarian tumors; Prostate cancer; Muscle tissue cancers such as Acute quadriplegic myopathy; Skin cancers such as Melanoma, Sarcoma, Kaposi sarcoma; Alveolar rhabdomyo sarcoma, Embryonal rhabdomyo sarcoma, Leiomyosarcoma; Germ cell tumors such as of the testes, testicular cancer; and Thyroid cancer such as Thyroid adenocarcinoma.

Embodiment 61. The pharmaceutical composition of embodiment 59, wherein the solid organ cancer is a liver cancer.

Embodiment 62. The pharmaceutical composition of embodiment 61, wherein the liver cancer is selected from the group consisting of hepatic cell carcinoma (HCC), fibrolamellar HCC, cholangiocarcinoma (bile duct cancer) and angiosarcoma.

Embodiment 63. The pharmaceutical composition of any one of embodiments 54-62, wherein the sphingosine-1-phosphate receptor agonist at least substantially does not agonize sphingosine-1-phosphate receptors other than types-1 and -5.

Embodiment 65. The pharmaceutical composition of any one of embodiments 54-64, wherein the sphingosine-1-phosphate receptor agonist includes a sphingosine-1-phosphate receptor agonist disclosed in any of U.S. Pub Nos. 20110172202, 20130231326, and 20150299149.

Embodiment 66. The pharmaceutical composition of any one of embodiments 54-64, wherein the sphingosine-1-phosphate receptor agonist includes ozanimod or a pharmaceutically acceptable salt thereof.

Embodiment 67. The pharmaceutical composition of any one of embodiments 54-66, wherein said composition is for parenteral administration.

Embodiment 68. The pharmaceutical composition of embodiment 67, wherein said composition is for administration via injection, such as intravenous injection, intramuscular injection, or subcutaneous injection.

Embodiment 69. The pharmaceutical composition of any one of embodiments 54-66, wherein said composition is for non-parenteral administration.

Embodiment 70. The pharmaceutical composition of any one of embodiments 54-66, wherein said composition is for oral administration by ingestion.

Embodiment 71. The pharmaceutical composition of any one of embodiments 54-70, further including at least one pharmaceutically acceptable excipient.

Embodiment 72. The pharmaceutical composition of any one of embodiments 54-71, wherein said composition is a solid dosage form.

Embodiment 73. The pharmaceutical composition of embodiment 72, provided in a dosage form selected from the group consisting of a tablet, a capsule, and a gel cap.

Embodiment 74. The pharmaceutical composition of any one of embodiments 54-66, wherein said composition is for administration via the alimentary canal.

Embodiment 75. The pharmaceutical composition of any one of embodiments 54-74, further including a therapeutically effective amount of a sphingosine kinase type I inhibitor, such as one disclosed in U.S. Pat. Nos. 8,372,888 and/or 8,314,151, such as SK1-I, or a pharmaceutically acceptable salt thereof.

Embodiment 76. The pharmaceutical composition of any one of embodiments 54-74, for use in combination with a therapeutically effective amount of a sphingosine kinase type I inhibitor, such as one disclosed in U.S. Pat. Nos. 8,372,888 and/or 8,314,151, such as SK1-I, or a pharmaceutically acceptable salt thereof.

Embodiment 77. The pharmaceutical composition of any one of embodiments 54-76, further including a therapeutically effective amount of a cellular ceramide generation promoter, such as 6-[(2S,4R,6E)-4-Methyl-2-(methylamino)-3-oxo-6-octenoic acid]cyclosporin D (Valspodor; PSC833) or a pharmaceutically acceptable salt thereof.

Embodiment 78. The pharmaceutical composition of any one of embodiments 54-76, for use in combination with a therapeutically effective amount of a cellular ceramide generation promoter, 6-[(2S,4R,6E)-4-Methyl-2-(methylamino)-3-oxo-6-octenoic acid]cyclosporin D (Valspodor; PSC833) or a pharmaceutically acceptable salt thereof.

Embodiment 79. The pharmaceutical composition of any one of embodiments 54-78 for use in combination with a therapeutically effective amount of ceramide.

Embodiment 80. A method for inducing apoptosis of mammalian cancer cells, such as liver cancer cells, such as hepatocellular carcinoma (HCC) cells, including the step of:
contacting the mammalian cancer cells with an effective amount of a sphingosine-1-phosphate receptor agonist, such as an agonist of one or both of sphingosine-1-phosphate receptor-1 ($S1P_1$) and sphingosine-1-phosphate receptor-5 ($S1P_5$) such as any of those disclosed in U.S. Pub Nos. 20110172202, 20130231326, and 20150299149, such as ozanimod (RPC1063), or a pharmaceutically acceptable salt thereof.

Embodiment 81. Use of a sphingosine-1-phosphate receptor agonist, such as an agonist of one or both of sphingosine-1-phosphate receptor-1 ($S1P_1$) and sphingosine-1-phosphate receptor-5 ($S1P_5$) such as any of those disclosed in U.S. Pub Nos. 20110172202, and 20130231326, and 20150299149, such as ozanimod (RPC1063), or a pharmaceutically acceptable salt thereof, for inducing apoptosis of mammalian cancer cells, such as liver cancer cells, such as, hepatocellular carcinoma (HCC) cells.

For embodiments involving ceramide, the ceramide may, for example, be formulated/co-formulated in an acid stable lipid vesicle/particle composition as disclosed in U.S. Pub. No. 20140271824, which is hereby incorporated by reference in its entirety, and administered/co-administered, for example by injection, such as intravenous injection, or orally.

Any of the method of treatment/use embodiments set forth herein may further include the step of: co-administering one or more immune checkpoint inhibitors, which may be monoclonal antibodies (mABs). The immune checkpoint inhibitor may be selected from the group consisting of the following: PD-1 inhibitors such as mAbs Pembrolizumab (Keytruda®) and Nivolumab (Opdivo®); PD-L1 inhibitors such as mAbs Atezolizumab (Tecentriq®), Avelumab (Bavencio®), and Durvalumab (Imfinzi®); and CTLA-4 inhibitors such as mAb Ipilimumab (Yervoy®); and V-domain Ig Suppressor of T Cell Activation (VISTA) inhibitors such as mAb JNJ-61610588 (ImmuNext Inc.). Similarly, any of the pharmaceutical composition embodiments of the invention may be for use in combination with one or more immune checkpoint inhibitors, such as those disclosed herein.

Still another embodiment of the invention provides a method for treating a cancer or a myeoproliferative disorder (myeloproliferative neoplasm), such as any of those disclosed herein, for example, a liver cancer, in a mammalian subject, such as a human, including the step of:
co-administering to a mammalian subject in need of treatment for a cancer or myeloproliferative disorder, a therapeutically effective amount of:
(a) a sphingosine kinase type I inhibitor, such as one disclosed in U.S. Pat. Nos. 8,372,888 and/or 8,314,151, such as SK1-I, or a pharmaceutically acceptable salt thereof; and
(b) one or more immune checkpoint inhibitors, which may be monoclonal antibodies, such as one or more selected from the group consisting of: PD-1 inhibitors such as mAbs Pembrolizumab (Keytruda®) and Nivolumab (Opdivo®); PD-L1 inhibitors such as mAbs Atezolizumab (Tecentriq®), Avelumab (Bavencio®), and Durvalumab (Imfinzi®); and CTLA-4 inhibitors such as mAb Ipilimumab (Yervoy®); and V-domain Ig Suppressor of T Cell Activation (VISTA) inhibitors such as mAb JNJ-61610588 (ImmuNext Inc.).

Immune checkpoint inhibitors may, for example, be administered by injection in the dosages described herein and/or at the currently approved dosages for said inhibitors.

The amount of compound that is effective for the treatment or prevention of a condition, alone or in combination with other compounds, may be determined by standard techniques. In addition, in vitro and/or in vivo assays may optionally be employed to help identify optimal dosage ranges. The precise dose to be employed will also depend on, e.g., the route of administration and the seriousness of the condition, and can be decided according to the judgment of a practitioner and/or each patient's circumstances. In other examples thereof, variations will necessarily occur depending upon the weight and physical condition (e.g., hepatic and renal function) of the patient being treated, the affliction to be treated, the severity of the symptoms, the frequency of the dosage interval, the presence of any deleterious side-effects, and the particular compound utilized, among other things.

Administration may be as a single dose or as a divided dose. In one embodiment, an effective dosage is administered once per month until the condition is abated. In another embodiment, the effective dosage is administered once per week, or twice per week or three times per week until the condition is abated. An effective dosage may, for example, be administered at least once daily or at least or at least once every two-days, or at least once every three days, four days, five days, six days or seven days. In another embodiment, an effective dosage amount is administered about every 24 h until the condition is abated. In another embodiment, an effective dosage amount is administered about every 12 h until the condition is abated. In another embodiment, an effective dosage amount is administered about every 8 h until the condition is abated. In another embodiment, an effective dosage amount is administered about every 6 h until the condition is abated. In another embodiment, an effective dosage amount is administered about every 4 h until the condition is abated.

The therapeutically effective dose may be expressed in terms of the amount of the compound(s) or pharmaceutically acceptable salts thereof administered per unit body weight of the subject per day of treatment, or the total amount administered per day of treatment. A daily dose may, for example, be at least 0.005 mg/kg of body weight, at least 0.01 mg/kg of body weight, at least 0.025 mg/kg of body weight, at least 0.05 mg/kg of body weight, at least 0.1 mg/kg of body weight, at least 0.2 mg/kg of body weight, at least 0.3 mg/kg of body weight, at least 0.4 mg/kg of body weight, at least 0.5 mg/kg of body weight, at least 0.6 mg/kg of body weight, at least 0.7 mg/kg of body weight, at least 0.8 mg/kg of body weight, at least 0.9 mg/kg of body weight, at least 1 mg/kg of body weight, at least 1.5 mg/kg of body weight, at least 2 mg/kg of body weight, at least 2.5 mg/kg of body weight, at least 3 mg/kg of body weight, at least 3.5 mg/kg of body weight, at least 4 mg/kg of body weight, at least 4.5 mg/kg of body weight, at least 5 mg/kg of body weight, or at one of said doses. A total daily dose may, for example, be in the range of 0.005 mg/kg to 5 mg/kg or any subrange or value therein, such as 0.025 to 5 mg/kg body weight, such as 0.05 to 5 mg/kg body weight. A total daily dose may, for example be in the range of 0.1 mg to 1,000 mg total or any subrange or value therein, such as 0.1 mg to 1,000 mg, such as 0.1 mg to 100 mg, such as 0.1 mg to 50 mg, such as 0.5 mg to 50 mg, such as 1.0 mg to 50 mg, such as 5 mg to 50 mg, or 0.1 mg to 10 mg, such as 0.5 mg to 10 mg. For SK1-I and related SphK1 inhibitors disclosed U.S. Pat. Nos. 8,372,888 and 8,314,151, and pharmaceutically acceptable salts thereof, a daily dose for human subjects may, for example, also be in the range of 0.5 mg/kg to 5 mg/kg or any subrange or value therein, such as 1 mg/kg to 4 mg/kg, such as 1 mg/kg to 3 mg/kg, or, for example, a total daily dose of 5 mg to 50 mg or any subrange or value therein, such as 10 mg to 40 mg, such as 20 mg to 40 mg. For ozanimod and related sphingosine-1-phosphate receptor agonists disclosed in U.S. Pub Nos. 20110172202, 20130231326, and 20150299149, and pharmaceutically acceptable salts thereof, a daily dose for human subjects may, for example, also be in the range of 0.1 mg to 10 mg or any subrange or value therein, such as 0.1 mg to 5 mg, such as 0.5 to 5 mg, such as 0.5 mg to 2.5 mg, such as 0.5 mg to 1.5 mg. A pharmaceutical composition according to the invention may, for example, include a daily dose amount of the compound as set forth herein.

The duration of treatment by administration of a therapeutic compound or combination according to the invention may continue for a plurality of days, such as for at least one week, at least two weeks, at least three weeks, at least four weeks, at least two months, at least three months, at least four months, at least five months, at least six months, at least seven months, at least eight months, at least nine months, at least 10 months, at least 11 months, at least 12 months, at least 1½ years, at least 2 years, at least three years, at least four years, or may continue indefinitely.

The terms co-administration and co-administering mean that each of the things being co-administered is administered to a subject in such temporal proximity that each (or its active metabolite(s)) is present in active form in the subject for an at least partially overlapping period of time. Accordingly, co-administration may include, simultaneous administration, such as when the things being administered are part of the same pharmaceutical composition, or sequential administration of the things being co-administered, for example, within the same day of each other, within 12 hours of each other, within 6 hours of each other, within 3 hours of each other, within 1 hours of each other, or within 15 minutes of each other. The things being administered may be administered by the same route, such as by oral ingestion or injection, or by different routes.

Pharmaceutically acceptable salts and the selection and preparation thereof are well known in the art. Such salts include but are not limited to hydrochloride, citrate, glycolate, fumarate, malate, tartrate, mesylate, esylate, cinnamate, isethionate, sulfate, phosphate, diphosphate, nitrate, hydrobromide, hydroiodide, succinate, formate, acetate, dichloroacetate, lactate, p-toluenesulfonate, pamitate, pidolate, pamoate, salicylate, 4-aminosalicylate, benzoate, 4-acetamido benzoate, glutamate, aspartate, glycolate, adipate, alginate, ascorbate, besylate, camphorate, camphorsulfonate, camsylate, caprate, caproate, cyclamate, laurylsulfate, edisylate, gentisate, galactarate, gluceptate, gluconate, glucuronate, oxoglutarate, hippurate, lactobionate, malonate, maleate, mandalate, napsylate, napadisylate, oxalate, oleate, sebacate, stearate, succinate, thiocyanate, undecylenate, and xinafoate.

It should be noted that the indefinite articles "a" and "an" and the definite article "the" are used in the present application to mean one or more unless the context clearly dictates otherwise. Further, the term "or" is used in the present application to mean the disjunctive "or" or the conjunctive "and." It should also be understood that wherever in the present application the term comprising or including (or a term of similar scope) is recited in connection with the description of any embodiment or part thereof, a corresponding embodiment or part thereof reciting instead the term consisting essentially of or the term consisting of (or a term of similar scope) is also disclosed.

All publications, patents, patent applications and other documents cited in this application are hereby incorporated by reference in their entireties for all purposes.

While various specific embodiments have been illustrated and described, it will be appreciated that various changes can be made without departing from the spirit and scope of the invention(s). Moreover, features described in connection with one embodiment of the invention may be used in conjunction with other embodiments, even if not explicitly exemplified in combination within.

What is claimed is:

1. A method for treating Acute lymphoblastic leukemia (ALL) in a mammalian subject, comprising the step of:
administering to a mammalian subject in need of treatment for Acute lymphoblastic leukemia (ALL) an effective amount of ozanimod or a pharmaceutically acceptable salt thereof.

2. The method of claim 1, wherein the administering step comprises administering the hydrochloride salt of ozanimod to the mammalian subject.

3. The method of claim 1, wherein the mammalian subject is a human.

4. The method of claim 3, wherein the administering step comprises administering the hydrochloride salt of ozanimod to the mammalian subject.

* * * * *